(12) United States Patent
Gallois et al.

(10) Patent No.: US 7,465,783 B2
(45) Date of Patent: Dec. 16, 2008

(54) PLANT PEPTIDE WITH ANTIMICROBIAL ACTIVITY

(75) Inventors: Patrick Gallois, Cheshire (GB); Valerie Hecht, Andorra la Vella (AD); Fabrice Varoquaux, Vinsa (FR); Robert Blanvillain, Berkeley, CA (US); Delphine Puertolas, Ramonville (FR); Valerie Delorme, Perpignan (FR); Dominique Roby, Pompertuzat (FR); Michel Delseny, Bompas (FR)

(73) Assignee: Centre National de la Recherche Scientifique, Paris (FR)

( * ) Notice: Subject to any disclaimer, the term of this patent is extended or adjusted under 35 U.S.C. 154(b) by 73 days.

(21) Appl. No.: 10/519,400

(22) PCT Filed: Jul. 4, 2003

(86) PCT No.: PCT/FR03/02077

§ 371 (c)(1),
(2), (4) Date: Nov. 23, 2005

(87) PCT Pub. No.: WO2004/005329

PCT Pub. Date: Jan. 15, 2004

(65) Prior Publication Data

US 2006/0168682 A1   Jul. 27, 2006

(30) Foreign Application Priority Data

Jul. 5, 2002   (FR) .................................. 02 08447

(51) Int. Cl.
C07K 14/00   (2006.01)
C07K 1/04   (2006.01)
C07K 14/415   (2006.01)
(52) U.S. Cl. ...................... 530/324; 530/345; 530/370; 514/12
(58) Field of Classification Search .................. None
See application file for complete search history.

(56) References Cited

U.S. PATENT DOCUMENTS 4,613,355 A   9/1986   Omura et al.

FOREIGN PATENT DOCUMENTS

WO   93/05153   3/1993
WO   WO9305153   *   3/1993

OTHER PUBLICATIONS

GenBank Accession No. AF118222 (1999).*
Alignment of SEQ ID No. 10 with AF118222.*
Falcon-Perez JM et al. 1999, J Biol Chem. 274:23584-90.*
Lazar et al. 1988, Mol. Cell. Biol. 8:1247-1252.*
Hill et al 1998, Biochem. Biophys. Res. Comm. 244:573-577.*
Guo et al. 2004, Proc. Natl. Acad. Sci. USA 101: 9205-9210.*
Laplant, Y. et al. "Arabidopsis thaliana BAC F3H7", retrieved from EBI, Database accession No. AF118222, XP002235082 1999.
Gallois, P. et al. "Arabidopsis thaliana RHN-binding protein (RBP37) gene, complete cds", retrieved from EBI, Database accession No. AF109721, XP002235081 1999.

* cited by examiner

*Primary Examiner*—Stuart F. Baum
*Assistant Examiner*—Li Zheng
(74) *Attorney, Agent, or Firm*—Oblon, Spivak, McClelland, Maier & Neustadt, P.C.

(57) ABSTRACT

The invention concerns novel peptides, in particular plant peptides, having an antimicrobial activity and a cytotoxic activity, in particular for plant cells. The invention also concerns polynucleotides coding for said peptides, vectors comprising said polynucleotides, micro-organisms and cells transformed with said vectors, transgenic organisms whereof all of part of the cells contain and/or express said vectors, uses of said peptides and said polynucleotides, in particular as plant-specific antimicrobial agents. The invention further concerns an antimicrobial and/or cytotoxic method for treating plants.

11 Claims, 5 Drawing Sheets

SEQUENCE LISTING

<160> NUMBER OF SEQ ID NOS: 32

<210> SEQ ID NO 1
<211> LENGTH: 16
<212> TYPE: PRT
<213> ORGANISM: Arabidopsis thaliana
<220> FEATURE:
<221> NAME/KEY: misc_feature
<222> LOCATION: (16)..(16)
<223> OTHER INFORMATION: Xaa is cysteine or serine

<400> SEQUENCE: 1

Met Trp Trp Leu Val Gly Leu Thr Pro Val Glu Leu Ile His Leu Xaa
1               5                   10                  15

<210> SEQ ID NO 2
<211> LENGTH: 17
<212> TYPE: PRT
<213> ORGANISM: Arabidopsis thaliana
<220> FEATURE:
<221> NAME/KEY: misc_feature
<222> LOCATION: (16)..(16)
<223> OTHER INFORMATION: Xaa is cysteine or serine

<400> SEQUENCE: 2

Met Trp Trp Leu Val Gly Leu Thr Pro Val Glu Leu Ile His Leu Xaa
1               5                   10                  15

Ala

<210> SEQ ID NO 3
<211> LENGTH: 18
<212> TYPE: PRT
<213> ORGANISM: Arabidopsis thaliana
<220> FEATURE:
<221> NAME/KEY: misc_feature
<222> LOCATION: (16)..(16)
<223> OTHER INFORMATION: Xaa is cysteine or histidine

<400> SEQUENCE: 3

Met Trp Trp Leu Val Gly Leu Thr Pro Val Glu Leu Ile His Leu Xaa
1               5                   10                  15

Ala Phe

<210> SEQ ID NO 4
<211> LENGTH: 19
<212> TYPE: PRT
<213> ORGANISM: Arabidopsis thaliana
<220> FEATURE:
<221> NAME/KEY: misc_feature
<222> LOCATION: (16)..(16)
<223> OTHER INFORMATION: Xaa is cysteine or serine

<400> SEQUENCE: 4

Met Trp Trp Leu Val Gly Leu Thr Pro Val Glu Leu Ile His Leu Xaa
1               5                   10                  15

Ala Phe Arg

<210> SEQ ID NO 5
<211> LENGTH: 20
<212> TYPE: PRT
<213> ORGANISM: Arabidopsis thaliana
<220> FEATURE:
<221> NAME/KEY: misc_feature
<222> LOCATION: (16)..(16)
<223> OTHER INFORMATION: Xaa is cysteine or serine

<400> SEQUENCE: 5

Met Trp Trp Leu Val Gly Leu Thr Pro Val Glu Leu Ile His Leu Xaa
1               5                   10                  15

Ala Phe Arg Glu
            20

<210> SEQ ID NO 6
<211> LENGTH: 21
<212> TYPE: PRT
<213> ORGANISM: Arabidopsis thaliana
<220> FEATURE:
<221> NAME/KEY: misc_feature
<222> LOCATION: (16)..(16)
<223> OTHER INFORMATION: Xaa is cysteine or serine

<400> SEQUENCE: 6

Met Trp Trp Leu Val Gly Leu Thr Pro Val Glu Leu Ile His Leu Xaa
1               5                   10                  15

Ala Phe Arg Glu Arg
            20

<210> SEQ ID NO 7
<211> LENGTH: 22
<212> TYPE: PRT
<213> ORGANISM: Arabidopsis thaliana
<220> FEATURE:
<221> NAME/KEY: misc_feature
<222> LOCATION: (16)..(16)
<223> OTHER INFORMATION: Xaa is cysteine or serine

<400> SEQUENCE: 7

Met Trp Trp Leu Val Gly Leu Thr Pro Val Glu Leu Ile His Leu Xaa
1               5                   10                  15

Ala Phe Arg Glu Arg Leu
            20

<210> SEQ ID NO 8
<211> LENGTH: 23
<212> TYPE: PRT
<213> ORGANISM: Arabidopsis thaliana
<220> FEATURE:
<221> NAME/KEY: misc_feature
<222> LOCATION: (16)..(16)
<223> OTHER INFORMATION: Xaa is cysteine or histidine
<220> FEATURE:
<221> NAME/KEY: misc_feature
<222> LOCATION: (23)..(23)
<223> OTHER INFORMATION: Xaa is cysteine or histidine

<400> SEQUENCE: 8

Met Trp Trp Leu Val Gly Leu Thr Pro Val Glu Leu Ile His Leu Xaa
1               5                   10                  15

Ala Phe Arg Glu Arg Leu Xaa
            20

<210> SEQ ID NO 9
<211> LENGTH: 24
<212> TYPE: PRT
<213> ORGANISM: Arabidopsis thaliana
<220> FEATURE:
<221> NAME/KEY: misc_feature
<222> LOCATION: (16)..(16)
<223> OTHER INFORMATION: Xaa is cysteine or serine
<220> FEATURE:
<221> NAME/KEY: misc_feature
<222> LOCATION: (23)..(23)

```
<223> OTHER INFORMATION: Xaa is cysteine or serine

<400> SEQUENCE: 9

Met Trp Trp Leu Val Gly Leu Thr Pro Val Glu Leu Ile His Leu Xaa
1               5                   10                  15

Ala Phe Arg Glu Arg Leu Xaa His
            20

<210> SEQ ID NO 10
<211> LENGTH: 25
<212> TYPE: PRT
<213> ORGANISM: Arabidopsis thaliana
<220> FEATURE:
<221> NAME/KEY: misc_feature
<222> LOCATION: (16)..(16)
<223> OTHER INFORMATION: Xaa is cysteine or histidine
<220> FEATURE:
<221> NAME/KEY: misc_feature
<222> LOCATION: (23)..(23)
<223> OTHER INFORMATION: Xaa is cysteine or histidine

<400> SEQUENCE: 10

Met Trp Trp Leu Val Gly Leu Thr Pro Val Glu Leu Ile His Leu Xaa
1               5                   10                  15

Ala Phe Arg Glu Arg Leu Xaa His Leu
            20                  25

<210> SEQ ID NO 11
<211> LENGTH: 48
<212> TYPE: DNA
<213> ORGANISM: Arabidopsis thaliana
<220> FEATURE:
<221> NAME/KEY: misc_feature
<222> LOCATION: (46)..(48)
<223> OTHER INFORMATION: nnn cysteine codon or serine codon

<400> SEQUENCE: 11
atgtggtggc tagttggact tacaccagtt gagttgatcc atcttnnn                48

<210> SEQ ID NO 12
<211> LENGTH: 51
<212> TYPE: DNA
<213> ORGANISM: Arabidopsis thaliana
<220> FEATURE:
<221> NAME/KEY: misc_feature
<222> LOCATION: (46)..(48)
<223> OTHER INFORMATION: nnn is a cysteine or serine codon

<400> SEQUENCE: 12
atgtggtggc tagttggact tacaccagtt gagttgatcc atcttnnngc a            51

<210> SEQ ID NO 13
<211> LENGTH: 54
<212> TYPE: DNA
<213> ORGANISM: Arabidopsis thaliana
<220> FEATURE:
<221> NAME/KEY: misc_feature
<222> LOCATION: (46)..(48)
<223> OTHER INFORMATION: nnn is a cysteine or serine codon

<400> SEQUENCE: 13
atgtggtggc tagttggact tacaccagtt gagttgatcc atcttnnngc attt         54

<210> SEQ ID NO 14
<211> LENGTH: 57
<212> TYPE: DNA
<213> ORGANISM: Arabidopsis thaliana
```

```
<220> FEATURE:
<221> NAME/KEY: misc_feature
<222> LOCATION: (46)..(48)
<223> OTHER INFORMATION: nnn is a cysteine or serine codon

<400> SEQUENCE: 14
atgtggtggc tagttggact tacaccagtt gagttgatcc atcttnnngc atttcga         57

<210> SEQ ID NO 15
<211> LENGTH: 60
<212> TYPE: DNA
<213> ORGANISM: Arabidopsis thaliana
<220> FEATURE:
<221> NAME/KEY: misc_feature
<222> LOCATION: (46)..(48)
<223> OTHER INFORMATION: nnn is a cysteine or serine codon

<400> SEQUENCE: 15
atgtggtggc tagttggact tacaccagtt gagttgatcc atcttnnngc atttcgagag     60

<210> SEQ ID NO 16
<211> LENGTH: 63
<212> TYPE: DNA
<213> ORGANISM: Arabidopsis thaliana
<220> FEATURE:
<221> NAME/KEY: misc_feature
<222> LOCATION: (46)..(48)
<223> OTHER INFORMATION: nnn is a cysteine or serine codon

<400> SEQUENCE: 16
atgtggtggc tagttggact tacaccagtt gagttgatcc atcttnnngc atttcgagag     60
cgt                                                                   63

<210> SEQ ID NO 17
<211> LENGTH: 66
<212> TYPE: DNA
<213> ORGANISM: Arabidopsis thaliana
<220> FEATURE:
<221> NAME/KEY: misc_feature
<222> LOCATION: (46)..(48)
<223> OTHER INFORMATION: nnn is a cysteine or serine codon

<400> SEQUENCE: 17
atgtggtggc tagttggact tacaccagtt gagttgatcc atcttnnngc atttcgagag     60
cgtctc                                                                66

<210> SEQ ID NO 18
<211> LENGTH: 69
<212> TYPE: DNA
<213> ORGANISM: Arabidopsis thaliana
<220> FEATURE:
<221> NAME/KEY: misc_feature
<222> LOCATION: (46)..(48)
<223> OTHER INFORMATION: nnn is a cysteine or serine codon
<220> FEATURE:
<221> NAME/KEY: misc_feature
<222> LOCATION: (67)..(69)
<223> OTHER INFORMATION: nnn is a cysteine or serine codon

<400> SEQUENCE: 18
atgtggtggc tagttggact tacaccagtt gagttgatcc atcttnnngc atttcgagag     60 cgtctcnnn                                                             69

<210> SEQ ID NO 19
<211> LENGTH: 72
<212> TYPE: DNA
```

<213> ORGANISM: Arabidopsis thaliana
<220> FEATURE:
<221> NAME/KEY: misc_feature
<222> LOCATION: (46)..(48)
<223> OTHER INFORMATION: nnn is a cysteine or serine codon
<220> FEATURE:
<221> NAME/KEY: misc_feature
<222> LOCATION: (67)..(69)
<223> OTHER INFORMATION: nnn is a cysteine or serine codon

<400> SEQUENCE: 19
atgtggtggc tagttggact tacaccagtt gagttgatcc atcttnnngc atttcgagag    60
cgtctcnnnc at                                                       72

<210> SEQ ID NO 20
<211> LENGTH: 75
<212> TYPE: DNA
<213> ORGANISM: Arabidopsis thaliana
<220> FEATURE:
<221> NAME/KEY: misc_feature
<222> LOCATION: (46)..(48)
<223> OTHER INFORMATION: nnn is a cysteine or serine codon
<220> FEATURE:
<221> NAME/KEY: misc_feature
<222> LOCATION: (67)..(69)
<223> OTHER INFORMATION: nnn is a cysteine or serine codon

<400> SEQUENCE: 20
atgtggtggc tagttggact tacaccagtt gagttgatcc atcttnnngc atttcgagag    60
cgtctcnnnc atctc                                                    75

<210> SEQ ID NO 21
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 21
caagtaagct tgctcagttg                                               20

<210> SEQ ID NO 22
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 22
gctctagata cttagagatg acagagacg                                     29

<210> SEQ ID NO 23
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 23
actgagctcg ttgtattttt aatcgaatgg                                    30

<210> SEQ ID NO 24
<211> LENGTH: 31
<212> TYPE: DNA
<213> ORGANISM: Artificial Sequence
<220> FEATURE:
<223> OTHER INFORMATION: synthetic oligonucleotide

```
<400> SEQUENCE: 24
acggaagctt tacttagaga tgacagagac g                                    31

<210> SEQ ID NO 25
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 25
cgtcttcgag aaaagtgtta g                                               21

<210> SEQ ID NO 26
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 26
atcagtcaga cagtcaaatt c                                               21

<210> SEQ ID NO 27
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 27
tacttagaga tgacagagac g                                               21

<210> SEQ ID NO 28
<211> LENGTH: 86
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<223> OTHER INFORMATION: Complementary oligonucleotide of SEQ ID NO: 29

<400> SEQUENCE: 28
gatcatgtgg tggctagttg gacttacacc agttgagttg atccatcttt gcgcatttcg     60
agagcgtctc tgtcatctct aatgca                                          86

<210> SEQ ID NO 29
<211> LENGTH: 78
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<223> OTHER INFORMATION: Complementary oligonucleotide of SEQ ID NO:28

<400> SEQUENCE: 29
ttagagatga cagagacgct ctcgaaatgc gcaaagatgg atcaactcaa ctggtgtaag     60
tccaactagc caccacat                                                   78

<210> SEQ ID NO 30
<211> LENGTH: 20
<212> TYPE: DNA
```

```
<213> ORGANISM: Artificial Sequence
<220> FEATURE:
<223> OTHER INFORMATION: synthetic oligonucleotide

<400> SEQUENCE: 30
cttcgtcaac atggtggagc                                                    20

<210> SEQ ID NO 31
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 31
ctagctagag gatcgatcc                                                     19

<210> SEQ ID NO 32
<211> LENGTH: 229
<212> TYPE: DNA
<213> ORGANISM: Arabidopsis thaliana

<400> SEQUENCE: 32
atcagtcaga cagtcaaatt cttgaattgg tcaatgttaa atttttaatt atcatgacaa        60
gtaaacttgc tcagttgtat ttttaatcga atggtaaata aactttaaag gatgaaattg       120
taatttgcaa gtatcacacg tcaagcgtat gtggtggcta gttggactta caccagttga       180
gttgatccat ctttgcgcat ttcgagagcg tctctgtcat ctctaagta                   229
```

PLANT PEPTIDE WITH ANTIMICROBIAL ACTIVITY

The present invention relates to novel isolated, natural or synthetic peptides, with antimicrobial activity, to the polynucleotides coding for said peptides, to the vectors comprising said polynucleotides, to the microorganisms and to the cells transformed with said vectors, to the nonhuman transgenic organisms of which all or part of the cells contain and/or express said vectors, to the uses of said peptides and said polynucleotides, particularly as specific antimicrobial agents of plants, as well as to a process of antimicrobial treatment of plants.

Peptides originating from plants with antimicrobial activity are known in the prior art. In this respect, it is possible to cite peptides with lytic activity such as the defensins, the cecropins, the thionines, the mellitins, originating from mammals or alternatively the defensins, the magainins, the attacins, the dipterins, the sapecins, the caerulins, the xenopsins, isolated from insects. Hybrids of these peptides have likewise been described.

Peptides from rabbits have likewise been described for their antimicrobial activity, as well as peptides with hydrolytic activity such as chitinase or β-1,3-glucanase.

Among the peptides originating from plants, it is possible to cite those described in the patents U.S. Pat. Nos. 6,147,281, 6,150,588 or alternatively U.S. Pat. No. 5,424,395.

The patent U.S. Pat. No. 6,147,281 describes peptides having antimicrobial activity on the pathogens of plants, present in etiolated barley leaves. These peptides particularly have an activity against *Corynebacterium sepedonicum.*

The patent U.S. Pat. No. 6,150,588 describes peptides having antimicrobial activity on the pathogens of plants and which can be isolated from berries of *Aralia* or of *Impatiens.*

U.S. Pat. No. 5,424,395 describes peptides derived from magainin 2 having antimicrobial activity on the pathogens of plants.

The peptides normally present in the plants and having an antimicrobial activity form a particularly interesting class of agents of biological combat against the pathogenic agents.

The identification of novel compounds derived from plants, capable of having a specific antimicrobial activity with respect to plants allows the development of novel biopesticides to be envisaged which constitute a reservoir of products in the case of appearance of resistance. It is in this context that the present invention is situated.

In a surprising and unexpected manner the inventors have isolated in *Arabidopsis thaliana* a peptide which has the peculiarity of having an antimicrobial activity, particularly against the pathogenic agents of plants. In its antimicrobial activity, said peptide has an at least bacteriostatic, possibly bactericidal, activity. Very particularly, said peptide has a specific antimicrobial activity of certain bacterial species, particularly of pathogenic species of plants, such as, for example, *Xanthomonas campestris, Pseudomonas syringae* or alternatively *Erwinia amylovora.*

The antimicrobial activity can be manifested in the form of two distinct actions: "microbicidal" (bactericidal, virucidal or fungicidal) inhibition, which consists in killing said microorganisms; and "microbiostatic" (bacteriostatic, virostatic or fungistatic) inhibition which consists in reducing or in inhibiting the proliferation capacities of said microorganisms.

Consequently, the invention relates to an isolated, natural or synthetic peptide, comprising at least any one of the following sequences SEQ ID NO : 1 to SEQ ID NO : 10:

SEQ ID NO: 1: Met-Trp-Trp-Leu-Val-Gly-Leu-Thr-Pro-Val-Glu-Leu-Ileu-His-Leu-$R_1$ SEQ ID NO: 2: Met-Trp-Trp-Leu-Val-Gly-Leu-Thr-Pro-Val-Glu-Leu-Ileu-His-Leu-$R_1$-Ala SEQ ID NO: 3: Met-Trp-Trp-Leu-Val-Gly-Leu-Thr-Pro-Val-Glu-Leu-Ileu-His-Leu-$R_1$-Ala-Phe SEQ ID NO: 4: Met-Trp-Trp-Leu-Val-Gly-Leu-Thr-Pro-Val-Glu-Leu-Ileu-His-Leu-$R_1$-Ala-Phe-Arg SEQ ID NO: 5: Met-Trp-Trp-Leu-Val-Gly-Leu-Thr-Pro-Val-Glu-Leu-Ileu-His-Leu-$R_1$-Ala-Phe-Arg-Glu SEQ ID NO: 6: Met-Trp-Trp-Leu-Val-Gly-Leu-Thr-Pro-Val-Glu-Leu-Ileu-His-Leu-$R_1$-Ala-Phe-Arg-Glu-Arg SEQ ID NO: 7: Met-Trp-Trp-Leu-Val-Gly-Leu-Thr-Pro-Val-Glu-Leu-Ileu-His-Leu-$R_1$-Ala-Phe-Arg-Glu-Arg-Leu SEQ ID NO: 8: Met-Trp-Trp-Leu-Val-Gly-Leu-Thr-Pro-Val-Glu-Leu-Ileu-His-Leu-$R_1$-Ala-Phe-Arg-Glu-Arg-Leu-$R_2$ SEQ ID NO: 9: Met-Trp-Trp-Leu-Val-Gly-Leu-Thr-Pro-Val-Glu-Leu-Ileu-His-Leu-$R_1$-Ala-Phe-Arg-Glu-Arg-Leu-$R_2$-His SEQ ID NO: 10: Met-Trp-Trp-Leu-Val-Gly-Leu-Thr-Pro-Val-Glu-Leu-Ileu-His-Leu-$R_1$-Ala-Phe-Arg-Glu-Arg-Leu-$R_2$-His-Leu in which $R_1$ and $R_2$ represent, independently or simultaneously, a cysteine or a serine.

The peptide according to the invention comprises at least the sequence SEQ ID NO : 1.

According to an advantageous embodiment of the invention, said peptide corresponds to any one of the sequences SEQ ID NO : 1 to SEQ ID NO : 10, such as defined above.

Isolated is understood here as meaning any peptide of whatever origin it may be, which has, starting from its source, undergone at least one enrichment step. Thus, the invention covers crude extracts, for example of vegetables or of vegetables cells, containing at least one peptide according to the invention, as well as forms of the latter which are much more pure.

In an advantageous manner, the peptide according to the invention can be either isolated from plants (*Arabidopsis thaliana,* for example) or obtained by chemical synthesis or alternatively by biotechnological means as, for example, starting from microorganisms, cells of plants or animals, or even modified organisms which do not normally express said peptide.

The invention likewise relates to an isolated peptide, whose sequence is substantially homologous to at least one of the sequences SEQ ID NO : 1 to SEQ ID NO : 10, such as defined above.

It is considered here that a peptide has a substantially homologous sequence when its sequence of amino acids has a similarity of at least 60% with the sequence of amino acids of at least one of the sequences SEQ ID NO : 1 to SEQ ID NO : 10 and that the peptide has conserved its initial antimicrobial activity, particularly its specific activity with respect to pathogenic microorganisms of plants.

A similarity of 60% between a peptide P and the sequences SEQ ID NO : 1 to 10 is understood as meaning that when the two peptides are aligned, 60% of the amino acids of P are identical to the corresponding amino acid of the sequences SEQ ID NO : 1 to 10, or are replaced by an amino acid of the same group.

An amino acid of the same group is understood as meaning an amino acid having more or less identical chemical properties. In particular, this term is understood as meaning amino acids having more or less the same charge and/or the same size, and/or the same hydrophilicity or hydrophobicity and/or the same aromaticity.

Such groups of amino acids especially include:
(i) glycine, alanine
(ii) isoleucine, leucine, valine
(iii) tryptophan, tyrosine, phenylalanine
(iv) aspartic acid, glutamic acid
(v) arginine, lysine, histidine
(vi) serine, threonine Other substitutions can be envisaged, in which an amino acid is replaced by another comparable but not natural amino acid (hydroxyproline, norleucine, ornithine, citrulline, cyclohexylalanine, dextrorotatory amino acids, etc.)

The fact that the peptide according to the invention has the antimicrobial properties described above allows its use as an antimicrobial agent, particularly directed against the pathogenic agents of plants, to be envisaged. Very particularly, the peptide according to the invention can be used as a bacteriostatic, possibly bactericidal, agent, still more particularly as a specific antimicrobial agent of *Xanthomonas campestris*, of *Pseudomonas syringae* or alternatively of *Erwinia amylovora*. That allows its use as a biopesticide not having toxic secondary effects on the environment to be envisaged.

The invention likewise relates to the use of an isolated peptide, comprising or corresponding to at least any one of the sequences SEQ ID NO : 1 to SEQ ID NO : 10 as an antimicrobial agent, particularly directed against the pathogenic agents of plants.

According to an advantageous embodiment of said use, said peptide according to the invention is a bacteriostatic, possibly bactericidal, agent, and still more particularly a specific antimicrobial agent of *Xanthomonas campestris*, of *Pseudomonas syringae* or of *Erwinia amylovora*.

In a surprising manner, the inventors have shown that:
the peptides according to the invention comprising or corresponding to at least any one of the sequences SEQ ID NO : 1 to SEQ ID NO : 10, in which $R_1$ represents a serine, conserve their antimicrobial activity;
the peptides according to the invention comprising or corresponding to at least any one of the sequences SEQ ID NO : 2 to SEQ ID NO : 10, in which $R_1$ represents a cysteine or a serine and $R_2$ represents a cysteine, have a cytotoxic activity;
the peptides according to the invention comprising or corresponding to at least any one of the sequences SEQ ID NO : 8 to 10, in which $R_1$ represents a cysteine and $R_2$ represents a serine, have a greatly reduced cytotoxic, or even inhibited, activity; although the antimicrobial activity is conserved;
the peptides according to the invention comprising or corresponding to at least any one of the sequences SEQ ID NO : 8 to 10, in which $R_1$ and $R_2$ simultaneously represent a serine, have a cytotoxic activity.

The cytotoxic activity of the peptide according to the invention is lost when the peptide comprises or corresponds solely to the sequence SEQ ID NO : 1.

Consequently, the present invention likewise relates to the use of at least one peptide comprising or corresponding to at least one of the sequences SEQ ID NO : 2 to SEQ ID NO : 10, in which $R_1$ represents a cysteine or a serine and $R_2$ represents a cysteine, or when it comprises or it corresponds to at least one of the sequences SEQ ID NO : 8 to SEQ ID NO : 10, in which $R_1$ and $R_2$ simultaneously represent a serine, as a cytotoxic agent, particularly as a cytotoxic agent for plant cells.

The present invention likewise relates to the use of the peptide according to the invention comprising or corresponding to at least one of the sequences SEQ ID NO: 2 to SEQ ID NO : 10, in which $R_1$ represents a cysteine or a serine and $R_2$ represents a cysteine, or when it comprises or it corresponds to at least one of the sequences SEQ ID NO : 8 to SEQ ID NO : 10, in which $R_1$ and $R_2$ simultaneously represent a serine, as a herbicidal agent.

The invention also relates to the use of the peptide according to the invention when it comprises or it corresponds to at least one of the sequences SEQ ID NO : 8 to SEQ ID NO : 10, in which $R_1$ represents a cysteine and $R_2$ represents a serine, as a noncytotoxic antimicrobial agent, particularly directed against the pathogenic agents of plants.

In an advantageous manner, the carboxyl functions and free amines of the peptides according to the invention can be protected.

The customary protective groups are well known. For example, the peptide according to the invention can be a peptide for which whose sequence is substantially homologous to at least one of the sequences SEQ ID NO : 1 to SEQ ID NO : 10, and/or that for which the N-terminal amine group, and optionally the other amine groups present in the molecule, are in acylated (for example acetylated) form. More generally, the invention includes not only the addition salts of the peptide with organic carboxylic salts and the acetates, but also other addition salts such as, for example, the trifluoroacetates, as well as addition salts of the peptide with mineral acids, such as sulphates, hydrochlorides, etc. The invention likewise includes the salts resulting from the salification of the carboxylic group(s), and especially the salts of alkali metals or alkaline earth metals such as the salts of sodium or of calcium.

The invention likewise relates to a composition comprising at least one peptide comprising or corresponding to at least any one of the sequences SEQ ID NO : 1 to SEQ ID NO : 10, such as described above and at least one appropriate vehicle.

The composition according to the invention can be a composition for alimentary, pharmaceutical or veterinary use, (antimicrobial or preservative composition) or, of course, even a composition for agricultural use (biopesticide and/or weedkiller).

The invention likewise relates to an isolated, natural or synthetic, polynucleotide, characterized in that it comprises at least one sequence coding for at least one of the peptides according to the invention, with the exception of genomic deoxyribonucleic acid (DNA) of *Arabidopsis thaliana*.

According to an advantageous embodiment of said polynucleotide, it comprises at least one of the following sequences SEQ ID NO : 11 to SEQ ID NO : 20:

SEQ ID NO: 11: ATG TGG TGG CTA GTT GGA CTT ACA CCA
               GTT GAG TTG ATC CAT CTT $R_3$

SEQ ID NO: 12: ATG TGG TGG CTA GTT GGA CTT ACA CCA
               GTT GAG TTG ATC CAT CTT $R_3$ GCA

-continued

```
SEQ ID NO: 13:  ATG TGG TGG CTA GTT GGA CTT ACA CCA
                GTT GAG TTG ATC CAT CTT R3 GCA TTT

SEQ ID NO: 14:  ATG TGG TGG CTA GTT GGA CTT ACA CCA
                GTT GAG TTG ATC CAT CTT R3 GCA TTT
                CGA

SEQ ID NO: 15:  ATG TGG TGG CTA GTT GGA CTT ACA CCA
                GTT GAG TTG ATC CAT CTT R3 GCA TTT
                CGA GAG

SEQ ID NO: 16:  ATG TGG TGG CTA GTT GGA CTT ACA CCA
                GTT GAG TTG ATC CAT CTT R3 GCA TTT
                CGA GAG CGT

SEQ ID NO: 17:  ATG TGG TGG CTA GTT GGA CTT ACA CCA
                GTT GAG TTG ATC CAT CTT R3 GCA TTT
                CGA GAG CGT CTC

SEQ ID NO: 18:  ATG TGG TGG CTA GTT GGA CTT ACA CCA
                GTT GAG TTG ATC CAT CTT R3 GCA TTT
                CGA GAG CGT CTC R4

SEQ ID NO: 19:  ATG TGG TGG CTA GTT GGA CTT ACA CCA
                GTT GAG TTG ATC CAT CTT R3 GCA TTT
                CGA GAG CGT CTC R4 CAT

SEQ ID NO: 20:  ATG TGG TGG CTA GTT GGA CTT ACA CCA
                GTT GAG TTG ATC CAT CTT R3 GCA TTT
                CGA GAG CGT CTC R4 CAT CTC
``` in which $R_3$ and $R_4$ represent, independently or simultaneously, a cysteine codon or a serine codon.

According to an advantageous arrangement of this embodiment, the polynucleotide according to the invention corresponds to one of the sequences SEQ ID NO : 11 to SEQ ID NO : 20, in which $R_3$ and $R_4$ represent a cysteine codon or a serine codon.

The polynucleotide according to the invention can be in the form of a single-stranded or double-stranded deoxyribonucleic acid (DNA) or ribonucleic acid (RNA).

The polynucleotide according to the invention can be deduced from the sequence of any one of the peptides according to the invention and synthesized with the aid of a DNA synthesizer. The polynucleotide can likewise be obtained from DNA banks, particularly DNA banks of plant cells, very particularly from a DNA bank of *Arabidopsis thaliana* cells.

The invention likewise relates to a composition comprising, in an appropriate medium, at least one polynucleotide, such as described above, and at least one appropriate vehicle.

For the expression of said peptides according to the invention, the polynucleotides can advantageously be introduced into an appropriate vector.

The vector used can be any vector known from the prior art. Particularly, it is possible to cite as vectors which can be used according to the invention plasmids, viruses or alternatively bacteriophages.

Among the plasmids which can be used according to the invention, it is possible to cite those described by R. L. Rodriguez and D. T. Denhardt (A Survey of Molecular Cloning Vectors and Their Uses, Butterworths, Boston, 1998) or alternatively by J. Sambrook et al., (Molecular cloning, Cold Spring Arbor, 2001).

Particularly, the vectors pMOSBlue®, sold by Amersham, the vectors pGEM®-T and PGEM®-T easy sold by Promega or alternatively the plasmids of the type *Agrobacterium Ti* (H. De Greve et al., J. Mol. Appl. Genet., 1 (1982), 499-511) can advantageously be used.

Said vector can additionally contain all regulatory sequences required for the replication of the vector and/or the expression of the peptide encoded by the polynucleotide (promoter, termination sites, etc).

In a particularly advantageous construct, the polynucleotide according to the invention is placed under the dependence of an inducible promoter, thus rendering the synthesis of the peptide dependent on predefined conditions, for example environmental conditions, on the presence of a pathogenic agent or on a chemical agent.

The invention thus also relates to a vector comprising any one of the polynucleotides such as described above, comprising or corresponding to at least one of SEQ ID NO : 11 to SEQ ID NO : 20 in which $R_3$ and $R_4$ represent, independently or simultaneously, a cysteine codon or a serine codon.

The invention additionally relates to the use of a polynucleotide or of a vector such as described above for the preparation of a peptide according to the invention.

The invention also relates to a modified biological system in which at least one polynucleotide according to the invention or at least one vector of the invention has been introduced.

Such a biological system can be, for example, a microorganism, like a bacteria such as *Escherichia coli*, an endophyte like those described in the International Applications WO 90/13224, WO 91/10363, WO 87/03303, WO 94/16076 or alternatively the Patent Application EP-125468 or alternatively a yeast such as *Saccharomyces cerevisiae*, a cell like, for example, an insect cell, an animal cell or a plant cell.

The invention likewise relates to the use of the polynucleotide according to the invention and/or of the vector of the invention for the preparation of a biologically modified system, where this can be a microorganism, an endophyte, a yeast or a eukaryotic cell.

The invention also relates to a composition comprising at least one biological system such as described above and at least one appropriate vehicle.

The invention also relates to the use of at least one modified biological system such as described above or of a composition comprising at least one modified biological system such as described above as an antimicrobial agent, particularly directed against the pathogenic agents of plants, and/or as a cytotoxic agent.

The modified biological system can optionally additionally allow the secretion of the peptide according to the invention in a culture medium rendering its extraction and its purification easier.

The introduction of the polynucleotide and/or of the vector according to the invention into the host modified biological system can be effected by any known method, like, for example, transfection, infection, fusion, electroporation, microinjection or alternatively biolistics.

The invention also relates to a nonhuman transgenic organism, of which all or part of the cells contain the polynucleotide according to the invention or the vector of the invention, in a free or integrated form.

Particularly, the transgenic organism of the invention is a transgenic plant.

The transgenic plant can belong to any plant species, particularly to a plant species capable of being infected by *Xanthomonas campestris* and/or *Pseudomonas syringae* and/or *Erwinia amylovora*.

It is possible to cite by way of example, for *Xanthomonas campestris*, cabbage, lucerne, soy beans, cotton, peas, or alternatively grain; for *Erwinia amylovora*, pear trees, apple trees or alternatively potatoes and for *Pseudomonas syringae*, bananas, wheat or alternatively plants of the Citrus family.

The transgenic organism of the invention, particularly the transgenic plant, when it expresses the peptide according to the invention, has an improved resistance to pathogens, particularly to phytopathogens, very particularly to *Xanthomonas campestris* and/or *Pseudomonas syringae* and/or *Erwinia amylovora*.

The invention thus also relates to a nonhuman transgenic organism, particularly a transgenic plant having an improved resistance to pathogens, particularly to phytopathogens, very particularly to *Xanthomonas campestris* and/or *Pseudomonas syringae* and/or *Erwinia amylovora*.

Any method of transgenic organism preparation, particularly the methods applied to plants, can be used for the preparation of the transgenic organisms of the invention.

In this regard, it is possible to cite the methods described in Plant Gene Transfer and Expression Protocols—Methods in Molecular Biology (Humana Press, editor H. Jones, 1995, 49: 39-48) or alternatively those described by P. Gallois et al., in Plant Cell Electroporation and Electrofusion Protocols—Methods in Molecular Biology (Humana Press, editor J. A. Nickoloff, 1995, 55, 89-108).

The advantage of the transgenic organisms of the invention resides in the fact that they express the antimicrobial peptide of the invention in a constitutive manner.

The invention likewise relates to a polyclonal or monoclonal antibody, directed against at least one of the peptides according to the invention.

Any method of preparation of the antibodies known from the prior art can be employed in order to obtain the antibodies of the invention.

The invention additionally relates to a process for detection of the polypeptide according to the invention, characterized in that in a first step a medium capable of containing said peptide and an antibody according to the invention are contacted and in a second step the complexes formed by the antibody and the peptide are detected. This process is particularly interesting for detecting traces of biopesticides in a particular environment.

The invention likewise relates to a process of antimicrobial and/or cytotoxic treatment, in which an organism, particularly a plant, and at least one antimicrobial and/or cytotoxic agent chosen from at least one of the peptides such as described above and/or one of the vectors and/or one of the polynucleotides and/or one of the biological systems and/or a composition described above are contacted by any appropriate means (application, spreading, spraying, etc.)

In agriculture, the process of treatment of the invention can be applied according to any of the forms used in agriculture, as, for example, in a traditional fashion by external application in the field, for example by spraying or spreading of a liquid composition of the invention, in a seed coating additive or in a transgenic plant strategy.

Beside the preceding arrangements, the invention also comprises other arrangements which will be evident from the description which follows, which refers to examples of employment of the invention as well as to annexed drawings, in which.

Figure 5:
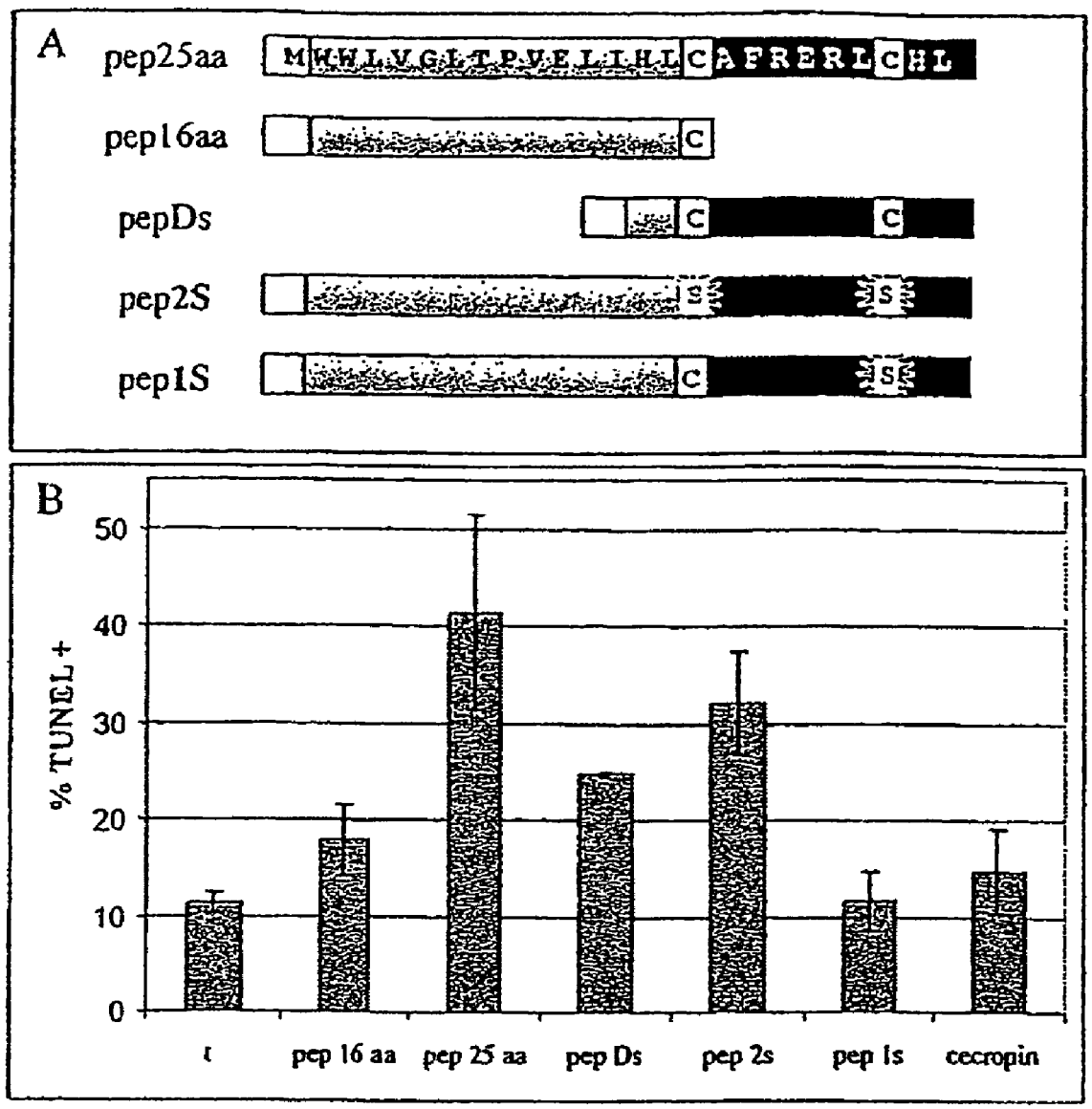

FIGS. 5A (SEQ ID NO :10) and 5B show the results of a TUNEL labeling experiment on protoplasts subjected to different variants of the peptide.

The following examples are illustrative of the invention and do not limit it in any way.

EXAMPLE 1

Material and Methods

1) Nomenclature:

SUP25 and pep25 designate the peptide of 25 amino acids corresponding to the sequence SEQ ID NO : 10.

SUP16 and pep16 designate the peptide of 16 amino acids corresponding to the sequence SEQ ID NO : 1.

PepDS designates a peptide SUP25 of which amino acids 4 to 15 have been removed.

Pep1S designates a peptide SUP 25 of which the cysteine in position 23 has been replaced by a serine.

Pep2S designates a peptide SUP 25 of which the cysteines in position 16 and 23 have each been replaced by a serine.

2) Plant Material

All the experiments were carried out on *Arabidopsis thaliana*. Two wild-type ecotypes were used:
   Columbia (Col-0) for all of the transformations by the in planta method.
   C24, an ecotype which has served for the construction of the promoter trap.

3) Bacterial Material
   *Escherichia coli*: strain DH5ct
   *Xanthomonas campestris* pv campestris: strain 8004
   *Pseudomonas syringae* pv tomato: strain DC3000
   *Erwinia amylovora*: strain 1430

4) Nucleic Material
   4.1. Plasmids
   4.1.a. Cloning Plasmids of PCR Fragments and of Digestion Products.

The plasmids which were used for cloning the PCR fragments by using the principle of "TA cloning" are pMOS-Blue®, sold by Amersham, the vectors pGEM®-T and pGEM®-T easy sold by Promega. These three vectors contain the gene conferring the resistance to ampicillin to bacteria which contain them. In addition, they carry the Gene lacZ which allows a selection of the plasmids which have effectively incorporated an insert. Their house is the bacterium *E. coli* (DH5α). These same plasmids, closed on themselves, or alternatively the vector pBluescript II SK® (PBSK, Stratagene) were used for the cloning of digestion products.

4.1.b. Cloning Plasmids Used as a Transitory Transformation Vector:

All the plasmids cited above can serve as a transitory expression vector.
   For the translational fusions, the plasmid used was pRTL2-EGFP (Restrepo A, Freed D D, Carrington J C., Nuclear transport of plant polyviral proteins. Plant Cell. 1990 October; 2(10): 987-98).
   For the construction of the sense and antisense expression cassettes of the protein SUP25, the PCR amplification of the gene or of the antisense gene is performed with the aid of the primers pepS-3X and peps-5H or pepAS-5S and pepAS-3H. The amplified fragment is cloned in pGEM®-T, the insert is excised by the restriction enzymes NcoI and NotI and then inserted in pRTL2-EGFP linearized by the same enzymes and purified on agarose gel.

4.2. Oligonucleotides

The sequences of the primers used are given below.

| No | Name | Sequence | Object |
|---|---|---|---|
| SEQ ID NO: 21 | pepS-5H | CAAGTAAGCTT GCTCAGTTG | Cloning of the ORF SUP25 in fusion with the operators in the binary vector |
| SEQ ID NO: 22 | pepS-3X | GCTCTAGATAC TTAGAGATGAC AGAGACG | Cloning of the ORF SUP25 in fusion with the operators in the binary vector |
| SEQ ID NO: 23 | pepAS-5S | ACTGAGCTCGT TGTATTTTAAT CGAATGG | Cloning of the anti-SUP25 in fusion with the operators in the binary vector |
| SEQ ID NO: 24 | pepAS-3H | ACGGAAGCTTT ACTTAGAGATG ACAGAGACG | Cloning of the anti-SUP25 in fusion with the operators in the binary vector |
| SEQ ID NO: 25 | OTi-05 | CGTCTTCGAGA AAAGTGTTAG | RT-PCR |
| SEQ ID NO: 26 | OEx-Ti-15 | ATCAGTCAGAC AGTCAAATTC | RT-PCR |
| SEQ ID NO: 27 | OPend3 | TACTTAGAGAT GACAGAGACG | RT-PCR |

Other commercial primers such as T7, T3, T7 term, SP6 and U19 were routinely used in the cloning experiments.

5) Culture Media and Solutions 5.1. Culture Media for Plants

MS germination medium: Murashige and Skoog medium with vitamin B5 (Duchefa) 2.2 g/l; MES (Sigma) 0.5 g/l; glucose 5 g/l; PH 5.7 with 1M KOH; plant agar 7 g/l (Duchefa).

5.2. Selection Media:

Antibiotics:
Kanamycin: 50 mg/l. (selects the neomycin phosphotransferase activity of the nptII gene).
Hygromycin: 30 mg/l. (selects the hygromycin phosphotransferase activity of the hpt gene).
Methotrexate: 0.1 mg/i (selects the dihydrofolate reductase activity of the dhfr gene).

5.3. Culture Media for *Escherichia coli:*
Liquid LB (Luria-Bertani) medium: yeast extract 5 g/l; bactotryptone 10 g/l; NaCl 10 g/l.
Liquid 2XL medium: yeast extract 10 g/l; bactotryptone 20 g/l; NaCl 1 g/l; glucose 2 g/l.
Liquid Terrific Broth medium: yeast extract 24 g/l; bactotryptone 12 g/l; glycerol 4 ml/l; $KH_2PO_4$ 4.62 g/l; $K_2HPO_4$ 25.08 g/l.
Solid media: as liquid media+15 g/l Bacto agar (Difco).

Antibiotics for *E. coli:* ampicillin: 100 mg/l; kanamycin: 50 mg/l; chloramphenicol (stock in ethanol): 12.5 mg/l.

5.4. Solutions and Buffers:

5.4.a. Buffers Relative to the Nucleic Acid

Extractions:
Plant genomic DNA extraction buffer:
Dellaporta method: Tris HCl (pH 8) 100 mM; EDTA (pH 8) 50 mM; NaCl 0.5 M; β-mercaptoethanol 10 mM.
Plant RNA extraction buffer (REB): Tris HCl (pH 8) 25 mM; EDTA (pH 8) 25 mM; NaCl 75 mM; SDS 1%.
TE buffer: Tris HCl (pH 8) 10 mM; EDTA (pH 8) 2 mM.

5.4.b. Buffers Relative to Electrophoreses in Agarose Gels:
DNA Gels
TBE buffer: Tris HCl 89 mM; boric acid 89 mM; EDTA (pH 8) 2 mM.
TAE buffer: Tris HCl 40 mM; acetic acid 40 mM; EDTA (pH 8) 1 mM.
10× DNA loading buffer: xylene cyanol FF 0.25%; bromophenol blue 0.25%; glycerol 30%.
RNA Gels
5× MOPS buffer: MOPS 0.1 M; sodium acetate 40 mM; EDTA (pH 8) 5 mM.
RNA loading buffer, per sample: 5× MOPS buffer 2 µl; formaldehyde 3.5 µl; formamide 10 µl; ethidium bromide (BEt) to 1 mg/ml 0.2 µl.

5.4.c. Buffers Relative to Hybridizations of Southern Blot Type
Depurination buffer: HCl 0.25 N.
Denaturation buffer: NaOH 0.5 N—NaCl 1.5 M.
20×SSC: NaCl 3 M; sodium citrate 0.3 M.
20×SSPE: NaCl 3.6 M; $NaH_2PO_4$ 0.2 M; EDTA (pH 7.7) 0.02 M.
Denhardt's 50×: Ficoll™ 10 g/l; PVP (polyvinyl-pyrrolidone) 10 g/l; BSA 10 g/l.
Hybridization buffer: EDTA 10 mM; 6× SSPE; SDS 0.5%; Denhardt's 5×.
Washing buffer I: 2×SSC; SDS 0.1%.
Washing buffer II: 1×SSC; SDS 0.1%.

5.4.d. Buffers Relative to the Study of the GUS Enzymatic Activity
Histochemistry
GUS coloration buffer: $KH_2PO_4$ 40 mM; $KHPO_4$ 60 mM, 5-bromo-4-chloro-3-indolylglucuronide (X-gluc, Biosynth AG, Switzerland) in solution in dimethylformamide (DMF) 1 mg/ml; sodium azide 0.02%; NaCl 50 mM; sodium ferricyanide 0.5 mM; sodium ferrocyanate 0.5 mM; Triton X 100 0.1% (v/v).
Spectrophotometry
GUS or GFP extraction buffer: Tris HCl (pH 7) 50 mM; SDS 0.1%; EDTA 10 mM; dithiothreitol (DTT) 3 mM.

5.4.e. Buffers for the Immunoimprints of Proteins
Extraction buffer for immunoimprints: Tris HCl (pH 8.3) 10 mM; NaCl 10 mM.
Loading buffer in acrylamide gel: Tris HCl (pH 6.8) 125 mM; SDS 4%; glycerol 10%; DTT 0.2 M; bromophenol blue 0.2%.
Coomassie Blue stain: Coomassie Blue R250 0.5 g/200 ml; 90% ethanol; 10% acetic acid.
Decolorizing solution: 10% ethanol; 10% acetic acid; 3.5% glycerol.
Transfer buffer: Tris base 20 mM; glycine 150 mM; 20% methanol (v/v)
TBS: Tris base 2.42 g/l; NaCl 8 g/l; adjusted to pH 7.6.
TRS-T: TBS+0.1% Tween 20.
Skimmed milk.

6) Methods:
  6.1) Methods of Plant Physiology
  6.1.1) Culture Conditions
  Soil Culture The soil cultures were carried out in a mixture of horticultural compost and of vermiculite, sterilized by autoclaving at 125° C for 20 minutes. The plants were cultivated in a culture chamber, at 20-22° C., in uninterrupted light.

In Vitro Culture

For in vitro culture, the seeds were sterilized under a laminar flow hood, by incubation in a sterilizing product (Domestos, Unilever) at 10% (v/v) in sterile distilled water, for 10 minutes. They are then rinsed 5 times in sterile distilled water. The seeds are then germinated in Petri dishes (20×100 mm) containing MS agar medium, with or without antibiotic. The plants were cultivated in a culture chamber, at 20-22° C., in uninterrupted daylight.

6.2) Methods of Molecular Biology
  6.2.1) Manipulation of the DNA
  6.2.1.A) Extraction Methods
  Plasmid DNA The bacterial plasmid DNA was extracted according to an alkaline lysis procedure and purified with the aid of two different kits according to the quantity of plasmid required: the kit "High Pure Plasmid Isolation Kit" of Boehringer Mannheim was used in order to carry out mini-preparations of plasmids (approximately 20 µg) from 5 ml of saturated culture (*E. coli* strain DH5α). This kit uses a silicone column in order to retain the DNA. The kit "Wizard™ Plus Midiprep DNA Purification System" of Promega was used in order to extract greater quantities of plasmid (approximately 100 µg for the plasmids with a large number of copies) from 50 ml of saturated culture (*E. coli* strain DH5α). This kit uses a column of guanidine hydrochloride in order to retain the DNA.

Genomic DNA

Dellaporta method: this method was employed in order to extract rapidly and easily numerous batches of genomic DNA intended for the PCR verification of the transgenic plants. This protocol, described by Dellaporta (Dellaporta et al., PMB, 1983, 1, 19-21), was adapted to smaller volumes in order to be realizable in 500 µl tubes. Each extract was obtained from 2 to 4 leaves (according to their size) of a single plant of *Arabidopsis thaliana*.

6.2.1.b) Polymerization Chain Reaction (PCR):

On plasmid or genomic DNA, after extraction:

The reactions are carried out in 500 µl tubes, in a final volume of 25 µl:

"mix": mixture of the following constituents, prepared for all the PCR reactions:

10 pmol of each of the two specific oligonucleotides,
11 µM of each dNTP,
2.5 µl of a 10× buffer, supplied by the Company marketing the polymerase,
1.25 mM of $MgCl_2$ (or $MgSO_4$, according to the enzyme used),
1 unit of thermostable DNA polymerase,
DNA matrix (function of the polymerase employed and of the type of DNA matrix),
qsp 25 µl of demineralized, deionized and sterile water.

For the conventional PCR reactions not necessitating the obtainment of a sequence product strictly identical to that of the matrix, the thermostable DNA polymerases Dynazyme (Ozyme), Taq (Promega) and Tfl (Promega) were used.

In this case, 5 ng of plasmid DNA or 200 ng of genomic DNA suffice for carrying out the experiment.

In order to obtain an amplified fragment whose sequence is identical to that of the matrix, the fidelity enzyme Pfu (Stratagene) was used. This enzyme requires a greater quantity of matrix: conventionally 100 to 150 ng of plasmid were used, according to the recommendations of the supplier. In the case of a genomic DNA matrix, 500 to 1000 ng were used.

Finally, when a PCR product of size greater than 2 kb was expected, PfuTurbo™ (Stratagene) was chosen. The quantities of DNA matrix used are then from 10 ng for plasmid DNA and approximately 500 ng for genomic DNA.

The reaction conditions are:

| Denaturation | 93° C., 3 min |
|---|---|
| Denaturation | 93° C., 1 min |
| Hybridization | between 48 and 55° C., 1 min |
| Elongation | 72° C., variable** |
| Final extension | 72° C., 10 min |

**variable according to the primer pair

Tfl and PfuTurbo™: 1 min/kb to be amplified
Pfu: 2 to 3 min/kb to be amplified

The number n of PCR cycles is between 30 and 40 for the reactions bringing into play Dynazyme (Ozyme), Taq (Promega) and Tfl (Promega). For the reactions carried out with the fidelity enzymes, the number of cycles is less (up to 25), so as to limit the errors.

On Plasmid DNA Contained in Bacterial Cells:

The amplification of a plasmid sequence can be carried out directly starting from bacterial colonies, this being in order to search the corresponding colonies for the recombinant bacteria (having effectively integrated the plasmid containing the insert of interest). The PCR "mix" (same composition as that given above) is prepared and distributed by 25 µl in several 500 µl tubes. The enzyme used is Dynazyme (Ozyme), Taq (Promega) or Tfl (Promega).

The colonies are selected at the surface of the solid culture medium with the aid of any appropriate selection tool (cone, magnifying glass, etc.), transplanted onto a new dish containing solid LB culture medium, and the selection tool is dipped into the "mix" and briefly agitated.

The PCR conditions are the same as those given above.

In all the cases, 10 µl of PCR product to which is added 1 µl of 10× DNA loading buffer deposited in an agarose gel (percentage of agarose variable as a function of the size of the amplified fragment to be observed, TBE buffer).

6.2.1.c) Cloning Methods:

Molecular cloning passes through different steps including the isolation of the fragment to be cloned (after action of a restriction endonuclease or not—case of PCR products to be cloned directly in a vector of "TA cloning" type—), the opening of the cloning vector (except in the case of vectors of "TA cloning" type), the ligation of these two elements and the amplification of the novel construct after its introduction into a bacterial cell.

Creation of the Recombinant Plasmid:

Hydrolysis by Restriction or Digestion Enzymes:

The restriction enzymes are used under the conditions recommended by the suppliers. The volume of enzyme used corresponds at most to 10% of the final volume of the digestion reaction.

Dephosphorylation of the Ends After Digestion:

The strategy of dephosphorylation has been used when it was necessary to prevent a vector digested by a sole restriction enzyme from closing on itself. In this case, the alkaline phosphatase of Boehringer Mannheim was employed according to the recommendations of the supplier.

Purification of DNA Fragments

The purifications of DNA fragments were carried out in 3 different ways according to the case:

Dialysis

When it was only a question of demineralizing the DNA (after action of a restriction endonuclease, for example), according to the case and the volume to be treated, a simple Millipore membrane, a "spin column" (Sephadex G-50) or alternatively a precipitation with ethanol followed by washing of the plug obtained with 70% ethanol was carried out.

Phenol/Chloroform

When more salts, elimination of the proteins (restriction enzyme or alkaline phosphatase) proved to be necessary, purification by the phenol/chloroform mixture followed by precipitation with ethanol was carried out.

Starting from an Agarose Gel

So as to separate the DNA fragment of interest from other contaminating DNA fragments, electrophoresis in agarose gel (TAE buffer) was carried out. The fragment of interest was then extracted from the gel with the aid of the kit "QIAQuick Gel Extraction Kit" of Qiagen or "Wizard™ PCR Prep" of Promega: the piece of agarose containing the DNA is rendered liquid by heating and then passed through a column which fixes the DNA. After a series of washes, the DNA is eluted with water and can then be used directly for cloning in a vector.

Ligation of the Insert and of the Vector:

The ligations between the DNA fragments to be integrated and the cloning vectors at the compatible sites were carried out in the presence of one unit of DNA ligase of the T4 phage (Promega or Boehringer Mannheim) preferentially at 16° C. for one night or else from 2 to 4 hours at ambient temperature. The total quantity of DNA used is between 200 ng and 500 ng, respecting a molar ratio between the vector and the insert of 1:3 to 1:5, in a final volume of 10 to 20 µl, corresponding to the conditions recommended by the supplier.

Ligation of an Adapter

The oligonucleotides are chosen in order to be paired leaving the desired cohesive ends. The oligonucleotides are hybridized at 1 pmol/µl in 10 µl of tfl 1× buffer. They are incubated for 1 min at 95° C. and then for 10 min at 45° C. Then 20 ng of oligonucleotides (in a maximum volume of 2 µl) and 100 ng of a vector are introduced into the ligation reaction.

Special Case of the Direct Cloning of a PCR Product

In the special case of the direct cloning of a product obtained by PCR, the enzymes Dynazyme (Ozyme), Taq (Promega) or Tfl (Promega) which have the peculiarity of adding from time to time an adenosine at the 3' ends of the double-stranded DNA are used. Ligation systems exploiting this peculiarity have been developed: they are pMOSBlue® (Amersham), pGEM®-T and pGEM®-T easy (Promega) systems, employing a vector digested by the enzyme EcoRV, generating blunt ends and addition of a thymidine to the 3' ends of the vectors. The linking between the PCR product, purified from an agarose gel, and the vector thus uses the so-called principle of "TA cloning". The ligation reaction is carried out in 10 µl, with the ligase supplied in the kit and according to the instructions of the manufacturer.

When the use of the fidelity enzymes Pfu or PfuTurbo™ (Stratagene)—which does not add adenosine again to the 3' ends of the amplified DNA—was required, the technique of "A-tailing" was employed: it consists in taking 3 µl of the PCR product obtained, in again adding to it 1 µl of 10× buffer, 1 µl of $MgSO_4$ at 25 mM, 1 µl of dATP at 2 mM, 1 µl of Tfl (at 5 units/µl) and 3 µl of demineralized, deionized and sterile water. The whole is incubated for 30 min at 70° C. and then dialyzed for 1 hour at ambient temperature against demineralized, deionized and sterile water. The fragment thus prepared is ready for direct use for the ligation reaction in a "TA cloning" vector.

Preparation and Transformation of Competent Bacteria

The plasmids are integrated by thermal shock following the protocol described by Sambrook et al. (Molecular cloning: a laboratory manual, 2nd Ed., 1989).

The recombinant bacteria are then detected by PCR amplification by means of primers present in the vector and/or the insert, according to the protocol described above.

6.2.1.d) Sequencing:

The sequence reactions were carried out by the chain extension termination method (Sanger et al., PNAS, 74, 5463-5467, 1977) in the presence of dideoxynucleotides, each labeled by a different fluorochrome (PRISM Read Reaction DyeDeoxy Terminator Cycle Sequence Kit, Applied Biosystems). Each reaction necessitates 250 ng of double-stranded DNA matrix and 5 pmol of primer in a final volume of 10 µl containing 4 µl of the Dye Deoxy Terminator mixture diluted 4 times. The reaction products were analysed by electrophoresis using an AB1377A sequencer.

6.2.1.e) Southern Blot Type Hybridization

Preparation of the Radioactive Probes

The probes used in the Southern blot type hybridization experiments were labeled with phosphorus 32 ($^{32}P$) by the PCR technique: it consists in incorporating $\alpha^{32}P$-dCTP (3000 Ci/mmol). The labeling by PCR is carried out in the following fashion: the reaction mixture, of a final volume of 25 µl, contains 2 ng of plasmid containing the probe, 2 pmol of each specific primer, 50 µCi of $\alpha^{32}P$-dCTP, 3.6 µM of cold dCTP, 60 µM of the other cold dNTPs and 1 µl of Tfl (at 5 units/µl). The PCR reactions are carried out as described above and comprise 20 to 25 cycles.

The quality of the probes obtained is tested on agarose gel transferred onto nylon membrane and exposed for 2 minutes on a radiographic film.

The radioactive probe is then purified on a column with the aid of the system MicroSpin7m G25 Columns (Amersham) before being used.

6.2.2) Manipulation of the RNA:

6.2.2.a) Extraction Method

The total RNAs were extracted from different tissues of Arabidopsis thaliana with the aid of the REB extraction buffer and according to the protocol of Kay et al. (Science, 236, 1299-1302, 1987). The polyA+ RNAs are obtained with the aid of a polyAtract kit (Promega) according to the indications of the supplier.

6.2.2.b) Hybridization of RNA: Northern blot

Preparation of Radioactive Probes

The probes used in the hybridization experiments of Northern blot type were labeled with phosphorus 32 by the PCR technique as described above.

Gel, Transfer to a Membrane and Hybridization

Up to 50 µg of total RNAs, in a volume of 4.5 µl, were added to 15.5 µl of loading buffer, and then denatured for 5 min at 65° C. They were deposited in an agarose gel at 1% (1× MOPS buffer, 2.2 M formaldehyde) and separated by electrophoresis in 1× MOPS buffer (5 min at 125 V, and then 2h30 at 75 V). The RNAs were stained with ethidium bromide in order to be sure of a homogeneous loading between the different tracks. After two passages of 15 min of the gel in the wash buffer, the RNAs were transferred for one night to nylon membranes (Hybond N+ membranes, Amersham) by capillarity (Sambrook et al., Molecular cloning: a laboratory manual, 2nd Ed., 1989) in the presence of a solution of SSC 20×. The RNAs were fixed to the membranes by incubation for 2 hours at 80° C. The pre-hybridization was carried out in 25 ml or 50 ml (following the size of the membranes) of hybridization buffer containing 20 mg/l of denatured calf thymus DNA. After 30 min to 2 h of prehybridization at 65° C., the denatured DNA probe is added to the buffer for an incubation of 16 h at 65° C. The membranes are then washed twice for 20 min at 65° C. with the wash buffer I. Then a last wash is carried out at 65° C. for 10 min maximum with the buffer II. The hybridization signals were detected either by exposure of BIOMAX™ film (Kodak) or by image analysis in the Phosphorimager (Storm 640, Molecular Dynamics). For successive hybridizations, the membranes were dehybridized according to the recommendations given in the Amersham manual.

6.2.2.c) RT-PCR Method

The PCR approach by reverse transcription has been used in this work in order to search, in the young siliques, for transcripts corresponding to the labeled DNA region. The method is divided into 2 successive steps: the obtainment of complementary DNA (cDNA) from total RNA, and then the PCR reaction, properly speaking, from these cDNAs.

Obtainment of cDNA

The reverse transcription reaction was carried out with the aid of the kit ProSTARTulirst-Strand RT-PCR Kit (Stratagene), from total RNAs treated with DNAs 1 (so as to limit the contamination of the future cDNAs by genomic DNA). The kit uses the reverse transcriptase of the Moloney murine leukaemia virus (MuMLV) and an oligodT primer.

PCR on the cDNAs

The reverse transcription products are used as a matrix for the PCR. The conditions are the same as those described above (cf. the paragraph concerning the PCR). The only difference resides in the final reaction volume (50 µl) and the rather high number of cycles (30 to 45 cycles according to the case).

EXAMPLE 2

Demonstration of an SUP25 Transcript

1) Demonstration of the Messenger Corresponding to the SUP25 Protein:

1.1) Extraction of the RNAs of *Arabidopsis thaliana:*

The total RNAs were extracted from different tissues of *Arabidopsis thaliana* with the aid of the REB extraction buffer and according to the protocol of Kay et al. (Science, 1987, 239: 1299-1302). The PolyA+ RNAs were obtained by using the polyAtract kit (Promega), according to the instructions of the supplier.

1.2) Northern Type Hybridization:

The conventional techniques of Northern type hybridization have never allowed the presence of the messenger corresponding to the protein SUP25 to be demonstrated in extracts of immature siliques of *Arabidopsis thaliana* (Varoquaux, thesis, University of Perpignan, France, 2000).

The level of expression of the corresponding native gene therefore appears below the detection threshold of the technique.

In order to increase the sensitivity of the experiment, the expression of the gene was analysed by the Northern technique on polyacrylamide gel with polyA+ RNA extracts. No hybridization signal could be observed on extracts of 4 µg testifying to the absence or to the very weak expression of the gene.

1.3) Polymerization Chain Reaction by Reverse Transcription (RT-PCR):

In order to search for a signal in the young siliques of *Arabidopsis thaliana,* the technique of reverse transcription RT-PCR is used.

The experiment is carried out in 2 steps: a reverse transcription of the total RNAs of siliques is carried out, followed by a PCR on the polyA+ cDNAs thus obtained.

1.3.a) Obtainment of Complementary DNA (cDNA):

The reverse transcription reaction was carried out with the aid of the kit ProSTARTulirst-Strand RT-PCR Kit (Stratagene), starting from 10 µg of total RNAs treated with DNAse 1 (so as to limit the contamination of the future cDNAs by the genomic DNA). The kit uses the reverse transcriptase of the Moloney murine leukaemia virus (MuMLV) and an oligodT primer.

Figure 1:
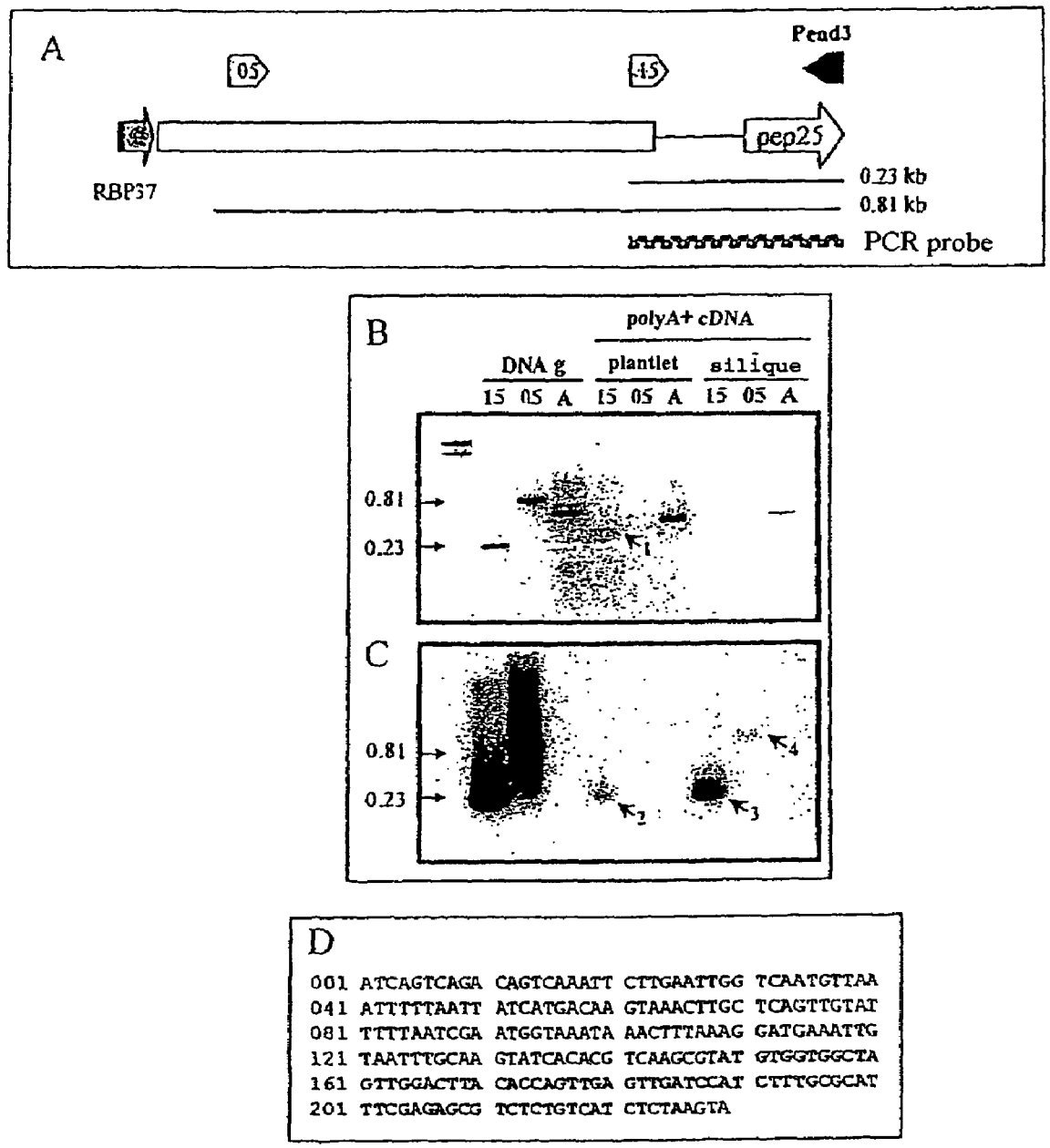
FIG. 1 shows the results obtained during a PCR amplification on the complementary DNAs obtained from RNA of young siliques of *Arabidopsis thaliana* (SEQ ID NO :32).

1.3.b) PCR on the cDNAs:

The 2 pairs of primers chosen (05, Pend3) and (15, Pend3) are shown in FIG. 1A.

The amplification on the genomic DNA (FIG. 1B, DNAg tracks 05 and 15) allows the size of the reaction products to be verified and the quality of amplification to be appreciated. The amplification products carried out with the aid of these 2 pairs must allow 2 fragments respectively of 0.23 kb (pair 15, Pend3) and of 0.81 kb (pair 05, Pend3) to be demonstrated.

The amplification of a ubiquitous actin 2 gene (tracks A) allows the level of amplification of the RNAs to be controlled and the contamination of genomic DNA by the presence of an intron between the 2 primers used to be evaluated.

2.5 µl of reverse transcription product (α) are used as a matrix for the PCR. The conditions are the same as those described above (cf. the paragraph concerning the PCR). The only difference resides in the final reaction volume (50 µl) and the rather high number of cycles (30 to 45 cycles according to the case).

The products obtained from the PCR reaction are then subjected to a hybridization according to Southern blotting after electrophoresis on agarose gel, with a radioactive PCR probe corresponding to the region of the peptide (FIG. 1A). The results of this hybridization are presented in FIG. 1C.

Some actin transcript shows that the level of RNA is very low in the extract of siliques with respect to the extract of plantlets (FIG. 1B).

The arrow 3 (FIG. 1C) reveals the presence of the amplification product with the predicted size of 0.23 kb attesting to the existence of the transcript in polyA+ RNA extracts of immature siliques; the arrow 4 shows a negligible signal with the expected size of 0.81 kb. The contamination of the extract by genomic DNA is thus very low.

The transcript of 0.23 kb is present in the extracts of immature siliques (0 to 5 days after fertilization), as well as in the plantlets at a lower level (FIG. 1C, arrow 2), if a comparison is made with actin.

Figure 4:
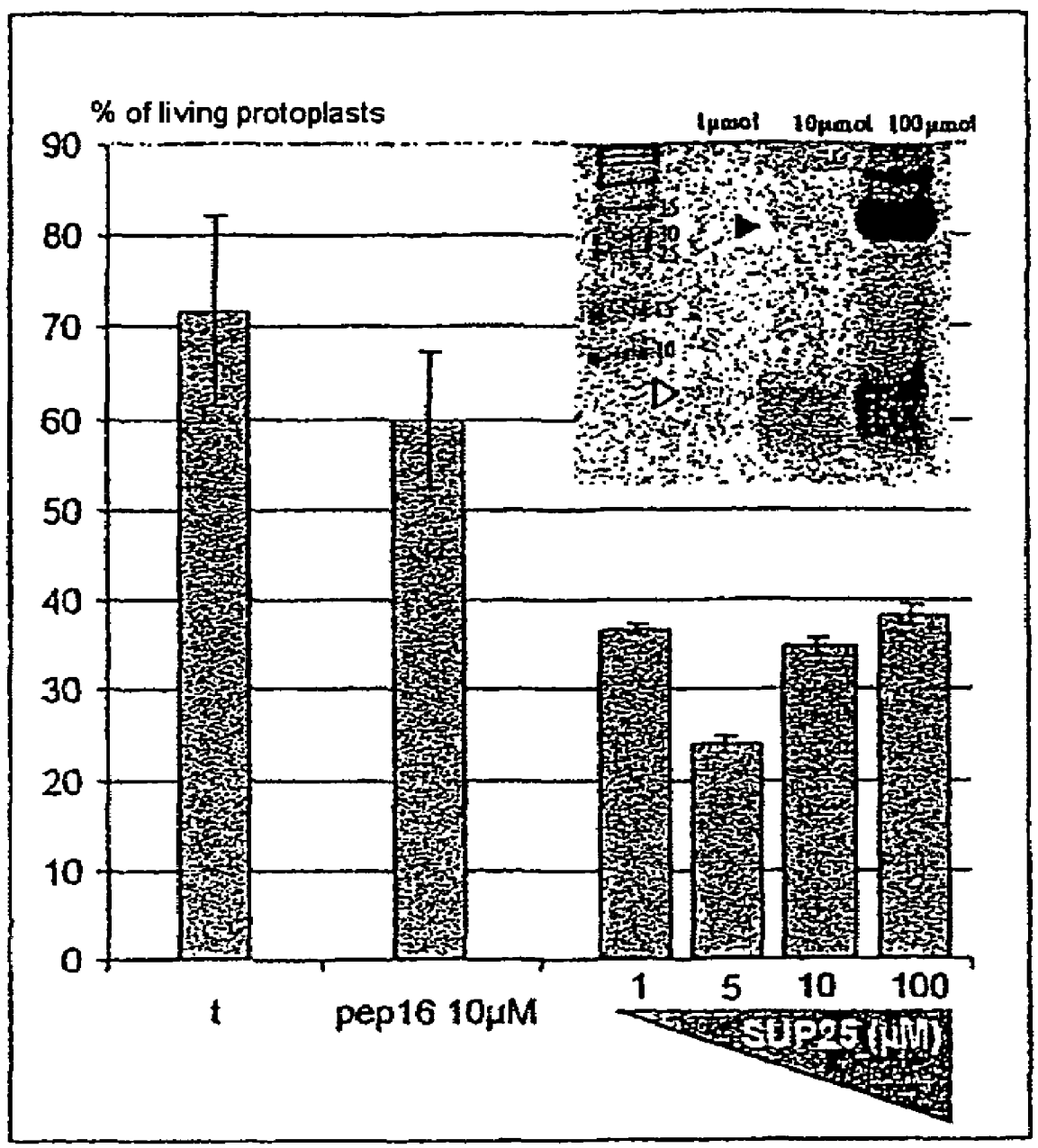
FIG. 4 shows the results of the tests carried out with a view to determining the optimum concentration for the cytotoxic activity of the peptide of 25 amino acids corresponding to the sequence SEQ ID NO : 10.

The presence of an artefactual band in FIG. 4B (arrow 1) is noted; this amplification product has been cloned and then sequenced and does not contain any homology with the gene of the invention; this band is additionally absent from the hybridization profile (FIG. 1C).

The sequencing of the product of 0.23 kb (SUP25 transcript) revealed a sequence of 227 base pairs shown in FIG. 1D.

2.) Demonstration of Functional ATGs in the Transcript:

The analysis of the sequence amplified by RT-PCR of the SUP25 transcript shows the existence of initiation codons (ATG) and thus of three open reading frames (ORF).

The sequence of amino acids deduced from the larger open reading frame corresponds to a peptide of 25 amino acids (SUP 25).

Figure 2:
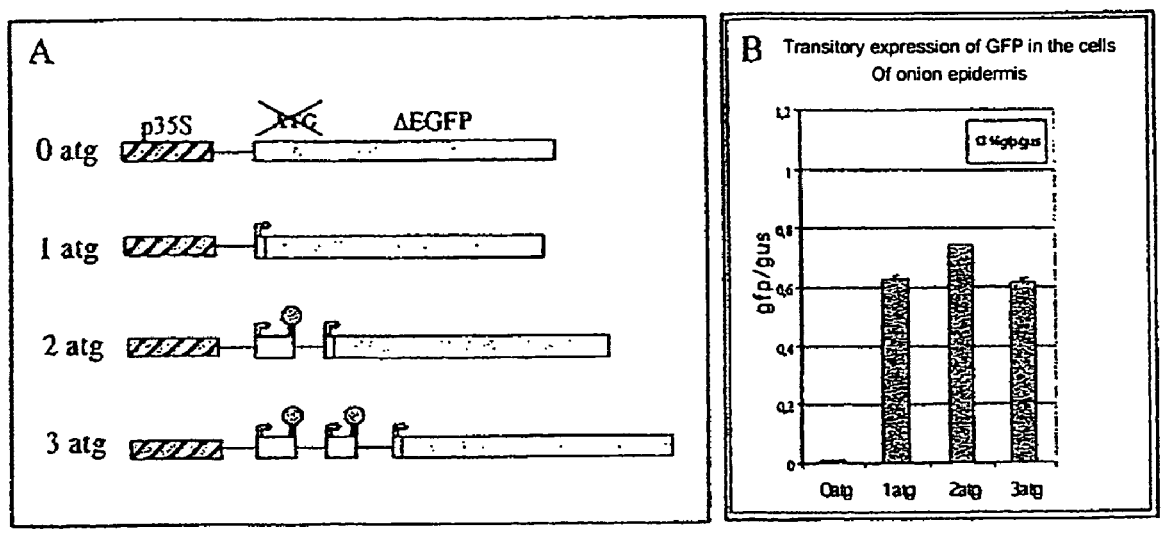
FIG. 2 shows the results of tests carried out with a view to demonstrating the functional initiation codon(s) (ATG) in the transcript SUP25. In panel 2A, the arrow indicates the position of ATG and the octagon the position of the stop codons.
Figure 3:
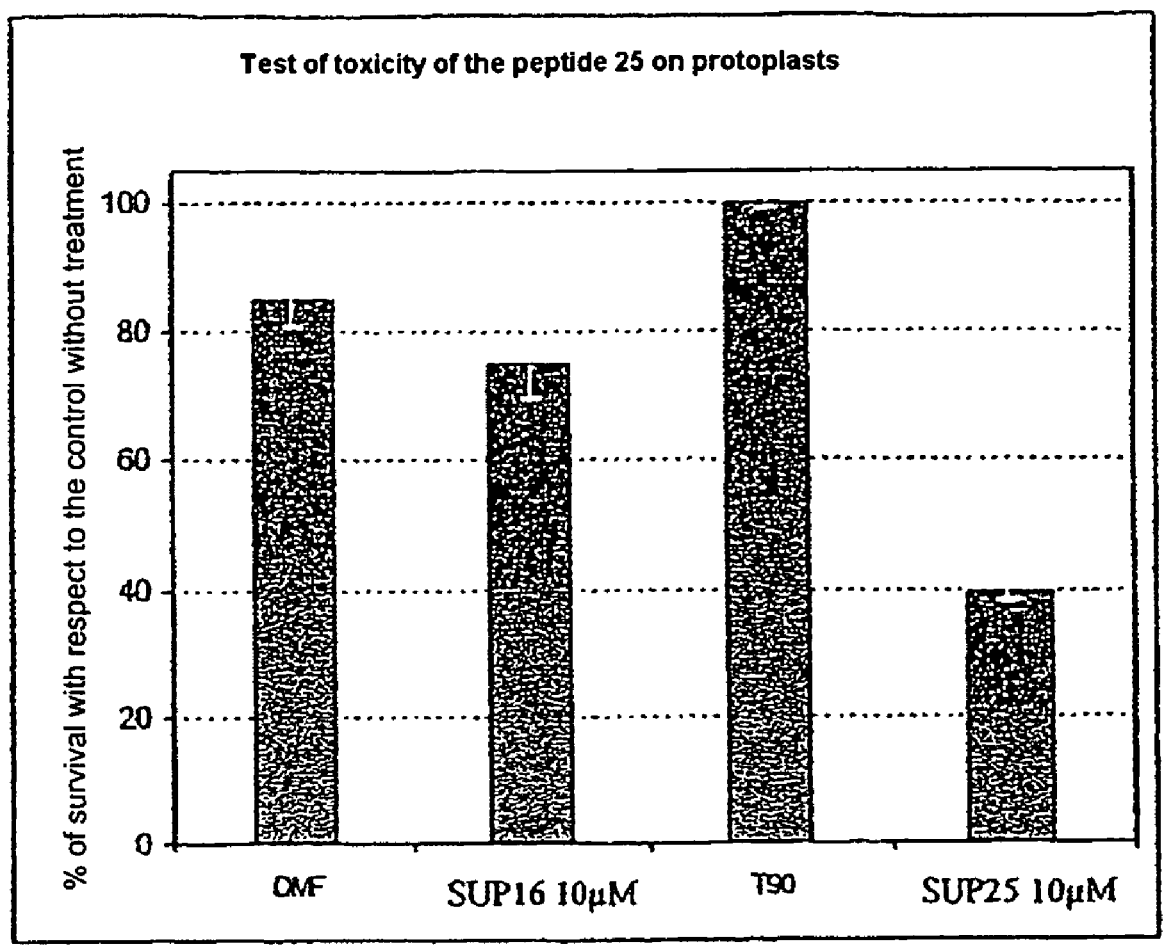
FIG. 3 shows the results of a phytotoxicity test of the peptide (SUP16) of 16 amino acids corresponding to the sequence SEQ ID NO : 1 and of the peptide (SUP25) of 25 amino acids corresponding to the sequence SEQ ID NO: 10.

In order to demonstrate the aptitude of the translational machinery to initiate the protein synthesis on the ATGs, a transitory expression experiment was conducted. The "Green Fluorescent Protein" (GFP) (PRTL2-EGFP plasmid) depleted of its initiation codon is cloned by translational fusion with the different ATGs (FIG. 2A, 0 atg: no ATG, 1 atg: 1 ATG, and so on). Each construct cloned in this way is cotransfected in the epidermis of onion with the plasmid pRTL2-GUS (Restrepo A, Freed D D., Carrington J C., Nuclear transport of plant polyviral proteins. Plant Cell. 1990 October; 2(10): 987-98) in a constant molar ratio, thus allowing to have available an internal control. On each sample, the subpopulation of cells expressing GFP is enumerated and then referred to the subpopulation expressing the protein GUS, each ratio of spots thus evaluated reflects the level of expression of the reporter gene (FIG. 2B). A first construct without ATG allows it to be verified, in a negative control, that the GFP without ATG is not translated, any cell expressing the GFP not being counted. For the three other translational fusions, the level of expression of the GFP is approximately the same, thus attesting to the functional character of the 3 ATGs. The presence of reading frames of small size upstream of the coding sequence does not affect the level of expression of the GFP. This indicates that the stop codons of the reading frames of small size do not impose the stopping of the ribosomal complex which is then capable of reinitiating the translation downstream on the transcript. In other terms, the result of this experiment demonstrates without ambiguity that the translation can be initiated or reinitiated on the third ATG of the locus. This result thus allows the hypothesis concerning the existence of the peptide to be supported.

EXAMPLE 3

Immunoimprints 3.1) Preparation of Antibodies Directed Against the Peptide:

The peptides were synthesized by Eurogentec. The antibodies were produced on the truncated synthetic peptide (sup 16) by Eurogentec.

3.2) Extraction of Proteins of Siliques:

The proteins were extracted by grinding of the siliques in the extraction buffer for immunoimprints, with the aid of mini-pilons (Kontes) connected to a grinder RZE2021 (Heidolph). After centrifugation (20 minutes at 10 000 g), the protein concentration of the supernatant was determined by the Bradford method with the aid of the reagent sold by Bio-Rad.

3.3) Electrophoretic Analyses:

The electrophoreses in polyacrylamide gel (SDS-PAGE) were carried out according to the method described by Laemmli (1970). The concentration gel is to 3% of an acrylamide/bis acrylamide mixture (30%/0.8%) and the separation gel is to 18% of the Prosieve mixture. 15 μg of total proteins, to which the loading buffer is added to the final concentration of 1×, are raised to 100° C. for 3 minutes and then deposited in each track.

The proteins are separated by a constant current of 15 to 20 mA per gel, for approximately 1 hour. The gels which are not intended for immunoimprints are stained with Coomassie Blue for 30 minutes and then destained until appearance of bands corresponding to the proteins.

3.4) Immunoimprints:

For the immunoimprints, the proteins were transferred after migration on the gel to nitrocellulose membranes (Pure Nitrocellulose membranes, 0.1 μm, Protan) in a Temblot Ae-6675 semi-dry electrotransfer tank (Touzart and Matignon) for 40 minutes under 2.5 mA.cm$^2$.

The labeling reactions were carried out at 37° C. under moderate stirring.

The membranes are incubated for 1 hour in 100 ml of TBS-T containing 5% of gelatine, and then washed with TBS-T (three times 15 minutes). The membranes are then incubated separately in the presence of 20 ml of TBS-T mixed with skimmed milk at 1.2% and 2 μl of the 1st antibody (serum recognizing Sup 16) for 2 hours. Then the membranes are washed in 200 ml of TBS-T (three times 15 minutes), and then incubated for 1 hour in 20 ml of TBS-T containing 1.2% of skimmed milk and 1 μl of the second antibody (goat antibody anti-rabbit IgG coupled to a radish peroxidase, Bio-Rad). The membranes are then washed in 200 ml of TBS-T (three times 15 minutes).

Visualization is done by means of the ECL kit "Western Blotting Detection Reagents" (Amersham), following the conditions recommended by the supplier.

EXAMPLE 4

Antimicrobial Activity of the Peptide

Toxicity experiments on the peptide of 25 amino acids (SUP 25) purified in the preceding example on different bacteria were carried out.

The different bacteria are cultured in 5 ml of LB medium or of medium appropriate to the strain, and then sedimented by centrifugation at 3000 g, and finally taken up in a volume of LB identical to the volume of bacteria. 50 μl of bacteria are inoculated into 9 ml of liquid TOPagar (LB+7 g/l of bactoagar) at 48° C. and rapidly poured into a square LB agar dish of 10 cm on each side. The drops of 10 μl of different concentrations of peptides are deposited on the solidified ToPagar. The dish is cultured for 16 hours.

Cecropin A at 20 μM, an insect peptide recognized as having antibacterial activity, serves as a positive control.

Results:

| Bacteria | Plant pathogen | Bacteriostatic activity | Active molarity | Cecropin A 20 μM |
|---|---|---|---|---|
| *Escherichia coli* Strain DH5α | No | Negative | — | Positive |
| *Xanthomonas campestris* pv *campestris* strain 8004 | Yes | Positive | 200 μM | Positive |
| *Pseudomonas syringae* pv tomato strain DC3000 | Yes | Positive | 20 μM | Positive |
| *Erwinia amylovora* Strain 1430 | Yes | Positive | 25 μM | Not tested |

The peptide of 25 amino acids does not have any activity on *Escherichia coli*, but has an activity on *Xanthomonas campestris*, *Pseudomonas syringae* and *Erwinia amylovora*, which allows its use as an antimicrobial agent particularly directed against pathogens of plants, very particularly at least against *Xanthomonas campestris, Pseudomonas syringae* and/or *Erwinia amylovora* to be imagined.

EXAMPLE 5

Cytotoxic Effect of the Peptide SUP 20 on Protoplasts of *Arabidopsis thaliana*

Toxicity tests carried out on isolated plant cells, without a wall, reveal a loss of viability induced by the addition of synthetic peptides to the culture medium. Certain mutations of the amino acid sequence of the peptide abolish the toxicity.

5.1) Measurement of the Viability by Staining with Fluorescein DiAcetate (FDA):

The tests of viability by staining with FDA rest on the detection of the esterase activity specifically present in the living cells. The FDA penetrates into the cell, the acetate residues are cleaved by the esterase activity and the fluorescein is liberated, conferring to the living cells a green coloration under blue excitation. As for the dead cells, when they are chlorophyll-containing, they fluoresce red owing to the pigments which they contain.

Protoplasts of leaves of *Arabidopsis thaliana* are obtained and cultured according to the method described by Danon and Gallois (FEBS letters, 1998, 437: 131-136).

The synthetic peptide of 25 amino acids (SUP25) is added to the protoplasts of leaves of *Arabidopsis thaliana* in culture.

A dose of 10 μM of SUP25 suffices to lower by a factor of 2.5 the viability of a cell population (FIG. 3).

In return, the truncated peptide of 16 amino acids (pep 16) at 10 μM only affects the proportion of living protoplasts by a factor 1.3.

Owing to the strong hydrophobicity of the peptide of 16 amino acids, it has been used in DiMethylFormamide (DMF) at 50%. The control DMF only affects the viability by a factor 1.2, which allows it to be said that the effect of the truncated peptide on the viability of protoplasts is very weak, or even nil, in comparison to the effect of the complete peptide.

It can thus be concluded that the toxicity of the peptide is specifically linked to the 10 amino acids of the C-terminal region of the peptide SUP25.

On the other hand, the dose involved in the effect corresponds to the orders of magnitude of lethal doses (1 to 100 μM) of different known antimicrobial peptides (Bulet P., Med.& Sc., 1999, 1, 23-9).

5.2) Determination of the Optimum Concentration for the Cytotoxic Activity of the Peptide:

Different concentrations of the peptide SUP25 (1 μM, 5 μM, 10 μM and 100 μM) were applied to the protoplasts of leaves of *Arabidopsis thaliana* (FIG. 4). At first sight, the activity of the peptide does not depend on the dose, although an optimum effect is observed at 5 μM. Because of the experimental procedure and in order not to add volumes which are too great to the protoplasts, the experiment was carried out using four stock solutions at the concentrations of 1 mM, 5 mM, 10 mM and 100 mM respectively.

In order to check the homogeneity of the stocks, an aliquot fraction, of the same volume for each peptide solution, was deposited on polyacrylamide gel in denaturing condition (FIG. 4, inset). At high concentration, the peptide is involved in the formation of multimeric complexes greater than 30 kDa. The stability of these complexes suggests the intervention of cysteines in the formation of disulfide bridges, only capable of resisting the SDS treatment.

This experiment shows that the monomeric form of the peptide is the most efficacious and that a concentration of 5 μM of the peptide leads to a very significant fall in viability.

5.3) Measurement of the Fragmentation of the DNA Following the Treatments with Different Modified Peptides:

This experiment has the aim of determining whether the effect of the peptide on the viability of the protoplasts of *Arabidopsis thaliana* corresponds to the cell necrosis or else to the implementation of the process of programmed cell death or apoptosis.

Apoptosis is distinguished from necrosis by a rigorous staging of death, punctuated by a set of genetically controlled events (Vaux and Korsmeyer (Cell, 1999, 96: 245-254); Pennell and Lamb (Plant Cell, 1997, 9: 1157-1168); Greenberg (P.N.A.S., 1996, 93: 12094-12097)). One of the steps is the fragmentation of the nuclear DNA which can be demonstrated by the TUNEL technique ("Terminal deoxynucleotidyl transferase-mediated dUTP Nick End Labeling") according to the protocol of Negoescu (Negoescu et al., Plant J., 1997, 13: 803-814). The TUNEL reaction allows the free 3'OH ends present in great quantity in the nuclei whose DNA is fragmented in the course of the process of apoptosis to be labeled. FIG. 5 shows the results of TUNEL labeling on protoplasts subjected to different variants of the peptide.

The external application of the peptide of 25 amino acids to protoplasts of Arabidopsis thaliana at 5 μM for 2 hours allows an increase in the population of positive TUNEL protoplasts to be observed (FIG. 5B). 4 times more nuclei show DNA fragmentation characteristics with respect to the control. The truncated peptide of 16 amino acids (pep16) does not induce any effect.

5.4) Study of the Biological Activity of Modified Peptides at the Level of the Cysteines:

5.4.1) Construction and Synthesis of the Modified Peptides:

In order to study the impact of the cysteines on the observed biological activity, the 3 modified peptides pepDs, Pep1S and Pep2S were synthesized (FIG. 5A) by Eurogentech.

5.4.2) Cytotoxic Activity of the Modified Peptides:

The fragmentation of the nuclear DNA induced by these modified peptides is demonstrated by the TUNEL technique (FIG. 5B).

pepDs has a residual activity.

Pep1S no longer has cytotoxic activity.

Pep2S has a cytotoxic activity.

This result suggests that the cysteines are involved in the formation of an intramolecular disulfide bridge thus allowing the peptide to remain free and active.

EXAMPLE 6

Obtainment of Transgenic Plants Expressing the Peptide SUP25

The sequence of the gene SUP25 can be introduced into an expression cassette using various promoters in order to control, at the transcriptional level, the production of the peptide in different types of plant cells.

6.1) Synthesis of the Sequence of the Gene:

Owing to the small size of the ORF, the sequence encoding the peptide SUP25 can be synthesized. A pair of sense and antisense oligonucleotides corresponding to the sequence of the peptide is custom-made synthesized. The sequence is conceived so that the hybridization of the pair of oligonucleotides leads the cohesive ends corresponding to restriction sites BamHI in 5' and PstI in 3' of the DNA fragment. The sites BamHI/PstI allow the gene to be cloned in the expression cassette of the plasmid pDH51 (Pietrzak M. et al., Expression in plants of two bacterial antibiotic resistance genes after protoplast transformation with a new plant expression vector. Nucleic Acids Res. 1986, 14 (14): 5857-68) in which the promoter CaMV 35S and the 3' region of the 35S directs the expression of the gene introduced.

Seq#1: (SEQ ID NO 28)
gatcATGTGGTGGCTAGTTGGACTTACACCAGTTGAGTTGATCCATCTTTG

CGCATTTCGAGAGCGTCTCTGTCATCTCTAAtgca

Seq#2: (SEQ ID NO 29)
TTAGAGATGACAGAGACGCTCTGAAATGCGCAAAGATGGATCAACTCA

ACTGGTGTAAGTCCAACTAGCCACCACAT

6.2) Ligation of the Sequence of the Peptide in an Expression Cassette

The oligonucleotides are hybridized at 1 pmol/µl in 10 µl of tfl 1× buffer (Sambrook J. et al., Molecular Cloning: A Laboratory Manual. Ed. CSHLP, 2001) and are incubated for 1 min at 95° C. and then 10 min at 45° C. Then, 20 ng of oligonucleotides (2 µl) are ligated in 100 ng of pDH51 vector using the BamHI/PstI sites (Sambrook et al., 2001). The ligation product is transformed in *E. Coli* XL1-B (Stratagene) by using a chemical method (Sambrook et al., 2001). The transformers are selected on the antibiotic ampicillin. The presence of the insert can be directly identified in the transformants by the absence of blue color in the medium containing the substrate X-GAL (Sambrook et al., 2001). Five independent transformants are used in order to extract the plasmid with the commercial kit High pure plasmid Isolation kit (Roche/Boehringer). The presence of the insert is verified by restriction with the enzyme EcoRI (Sambrook et al., 2001). The sequence fidelity of the constructs is verified for the presence of the sequence SUP25 by sequencing (Sambrook et al., 2001) by using a primer pairing the promoter 35S [op35S52: CTTCGTCAACATGGTGGAGC]: (SEQ ID NO : 30) or the terminator 35|S [oter35: CTAGCTAGAGGATCGATCC]: (SEQ ID NO : 31).

6.3) Transfer of the Transgene to a Binary Transformation Vector

The transgene is then subcloned in the site EcoRI of the T-DNA region of the binary plasmid pZP111 (Hajdukiewicz P., et al., The small, versatile pPZP family of *Agrobacterium* binary vectors for Plant transformation. Plant Mol Biol., 1994, (6): 989-94), containing a selection gene NPTII conferring to the plants resistance to the antibiotic kanamycin. The plasmid likewise contains a selection gene aadA for chloramphenicol selection in *E. Coli* or *Agrobacterium*. The ligation product is transformed in *E. Coli* XL1-B (Stratagene) by using a chemical method (Sambrook et al., 2001). The transformants are selected on LB medium (Sambrook et al., 2001)+25 mg/l of chloramphenicol. The presence of the insert in the plasmid pZP111 can be directly identified in the bacterial transformants by the absence of blue colour in the medium containing the substrate X-GAL (Sambrook et al., 2001).

6.4) Transfer of the Binary Vector into *Agrobacterium*.

A positive strain is selected, the plasmid is purified by using the kit commercial High pure plasmid Isolation kit (Roche/Boehringer). The disarmed strain of *Agrobacterium tumefaciens* C58C1 (Koncz C. and Schell, J., The promoter of TI-DNA gene 5 controls the tissue-specific expression of chaemeric genes carried by a novel type of *Agrobacterium* binary vector, Mol. Gen. Genet., 204: 383-396) is rendered competent and then transformed by electroporation (Shen W J. and Forde B G., Efficient transformation of *Agrobacterium* spp. by high voltage electroporation. Nucleic Acids Res. 1989, 17 (20): 8385) with the binary plasmid containing the constructs of T-DNA. After 3 days of culture at 28° C., the colonies resistant to chloramphenicol 25 mg/l, rifampicin 50 mg/l, gentamicin 25 mg/l, are confirmed positive by PCR using primers detecting the 35S promoter [op35S52: CTTCGTCAACATGGTGGAGC]: (SEQ ID NO : 30) and the terminator 35|S [oter35: CTAGCTAGAGGATC-GATCC]: (SEQ ID NO : 31) (Sambrook et al., 2001).

6.5) Obtainment of Transgenic Plants.

The transgenic plants are then obtained by agro-infection by using the strain C58C1 (Koncz C. and Schell, 1986) and the method of transformation of flower buds of *Arabidopsis thaliana* according to the protocol described by Bechtold, N. et al., (In planta *Agrobacterium* mediated gene transfer by infiltration of adult *Arabidopsis thaliana* plants, C.R. Acad. Sci. (1993) Paris, 316, 1194). Briefly, a preculture of 10 ml of YEP (yeast extract 10 g/l; peptone 10 g/l; glucose 20 g/l; kanamycin 50 mg/l; rifampicin 50 mg/l; gentamicin 25 mg/1) is inoculated with a colony of *Agrobacterium*. After 16 h with stirring at 28° C., 500 ml of YEP are cultured. When the culture attains an $OD_{600}$=0.8, the bacteria are harvested after centrifugation at 3000 g and dissolved in the infiltration medium (MS medium 2.16 g/l (Duchefa); MES (Sigma) 0.5 g/l; sucrose 5%; pH 5.7 adjusted with KOH; Silwet L-77 (Osi Specialises Ins.) 0.02%) at a final OD of 0.5.

The *Arabidopsis thaliana* plants, at the stage where the flower stalks begin to initiate the first flowers, are soaked in the infiltration solution for 10 minutes under vacuum (−1 atm) in a desiccator. The plants are then drained and then cultivated up to the harvesting of the seeds with the 2 first days of culture under plastic film. The seeds are harvested 4 weeks after infiltration. After a minimum of 15 days of storage, the seeds are sterilized by a solution of 70% ethanol, for 10 min and then selected in vitro on Gamborg B5 germination medium (Duchefa) 1.85 g/l and Phytagel (Sigma) 3 g/l containing 400 mg/l of the antibiotic kanamycin whose resistance is carried by the T-DNA. The resistant plants (approximately 1% of the seeds) are transplanted in soil, conserved under plastic for 4 days and cultivated up to the harvesting of the seeds.

The analysis of the number of insertion loci of the transgene is done by a statistical test of the Mendelian segregation of the selection gene, here for kanamycin, in vitro on Gamborg B5 germination medium (Duchefa) and Phytagel (Sigma) 3 g/l containing 400 mg/l of the antibiotic kanamycin. 10 plants with a sole insertion locus are selected (segregation 3:1). The presence of the transgene is confirmed in approximately 8 plants out of 10 by PCR analysis of purified DNA of the plants by the method (Dellaporta et al., Plant. Mol. Biol. Rept., 1983, 1, 19-21) and using primers detecting the 35S promoter [op35S52: CTTCGTCAACATGGTG-GAGC]: (SEQ ID NO : 30) and the terminator 35|S [oter35: CTAGCTAGAGGATCGATCC]: (SEQ ID NO : 31). The expression of the peptide is confirmed by western analysis (Sambrook et al., 2001) of the protein extract of the transgenic plants by using an antibody against the total sequence of the wild-type peptide SUP25 and the ECL detection kit (Amersham).

The invention claimed is:

1. An isolated peptide comprising SEQ ID NO : 10, in which the amino acid at position 16 and the amino acid at position 23 represent independently or simultaneously, a cysteine or a serine.

2. The peptide as claimed in claim 1, consisting of SEQ ID NO : 10.

3. The peptide as claimed in claim 1, wherein at least one amine and/or carboxylic, free functional group is protected by a protective group.

4. The peptide as claimed in claim 3, wherein the C-terminal carboxylic group and/or the other carboxylic groups present in the peptide are in the form of an ester or of an amide.

5. The peptide as claimed in claim 3, wherein the N-terminal amine group, and/or the other free amine groups present in the molecule, are in acylated form.

6. A composition comprising at least one peptide as claimed in claim 1 and at least one appropriate vehicle.

7. A composition comprising at least one peptide as claimed in claim 3 and at least one appropriate vehicle.

8. A composition comprising at least one peptide as claimed in claim 5 and at least one appropriate vehicle.

9. The peptide as claimed in claim 2, wherein at least one amine and/or carboxylic, free functional group is protected by a protective group.

10. The peptide as claimed in claim 9, wherein the C-terminal carboxylic group and/or the other carboxylic groups present in the peptide are in the form of an ester or of an amide.

11. The peptide as claimed in claim 10, wherein the N-terminal amine group and/or the other free amine groups present in the peptide are in acylated form.

* * * * *